(12) United States Patent
Sato et al.

(10) Patent No.: US 8,373,011 B2
(45) Date of Patent: Feb. 12, 2013

(54) PROCESS FOR PRODUCING SATURATED ALIPHATIC HYDROCARBON COMPOUND, AND LUBRICANT COMPOSITION

(75) Inventors: Haruhito Sato, Chiba (JP); Hideto Kamimura, Chiba (JP)

(73) Assignee: Idemitsu Kosan Co., Ltd., Tokyo (JP)

(*) Notice: Subject to any disclaimer, the term of this patent is extended or adjusted under 35 U.S.C. 154(b) by 585 days.

(21) Appl. No.: 11/980,382

(22) Filed: Oct. 31, 2007

(65) Prior Publication Data

US 2008/0146469 A1 Jun. 19, 2008

Related U.S. Application Data

(63) Continuation-in-part of application No. PCT/JP2006/308890, filed on Apr. 27, 2006.

(30) Foreign Application Priority Data

May 12, 2005 (JP) ................................. 2005-140220
Nov. 30, 2005 (JP) ................................. 2005-346533

(51) Int. Cl.
*C10M 105/04* (2006.01)
*C10M 169/04* (2006.01)
*F16C 33/00* (2006.01)

(52) U.S. Cl. ............. 585/16; 585/700; 508/110; 384/13; 384/100

(58) Field of Classification Search ..................... 585/16
See application file for complete search history.

(56) References Cited

U.S. PATENT DOCUMENTS 3,876,720 A * 4/1975 Heilman et al. ................ 585/16
3,907,922 A * 9/1975 Heilman et al. ............... 585/510
3,957,664 A * 5/1976 Heilman et al. ............... 508/110
4,658,078 A   4/1987 Slaugh et al.
(Continued)

FOREIGN PATENT DOCUMENTS

FR    1 330 081 A    6/1963
GB      961903       6/1964
(Continued)

OTHER PUBLICATIONS

U.S. Appl. No. 12/524,176, filed Jul. 23, 2009, Kamimura.

*Primary Examiner* — Ellen McAvoy
(74) *Attorney, Agent, or Firm* — Oblon, Spivak, McClelland, Maier & Neustadt, L.L.P.

(57) ABSTRACT

The present invention provides a process for producing a saturated aliphatic hydrocarbon prepared using an α-olefin as a raw material and represented by the general formula (1), including the steps of: (I) producing a vinylidene olefin by dimerizing the α-olefin in the presence of a metallocene complex catalyst; (II) further dimerizing the vinylidene olefin in the presence of an acid catalyst; and (III) hydrogenating the obtained dimer. Further, there are provided a lubricant composition containing the saturated aliphatic hydrocarbon compound produced by the above process, a bearing oil consisting of the lubricant composition, and making use of the same, a bearing and gyral equipment. The saturated aliphatic hydrocarbon compounds produced by the process of the present invention have low-temperature fluidity, exhibiting low evaporativity, and excellent in thermal stability and oxidation stability. Thus, the saturated aliphatic hydrocarbon compounds are suitable for use as, for example, a base oil of lubricant composition for hydraulic pressure, turbine, working machine, bearing, gear, metal-working, etc.

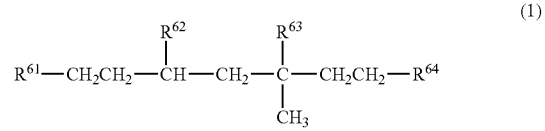

(1)

17 Claims, 2 Drawing Sheets

U.S. PATENT DOCUMENTS

| | | | |
|---|---|---|---|
| 5,053,569 A | 10/1991 | Marquis et al. | |
| 5,087,788 A | 2/1992 | Wu | |
| 5,095,172 A * | 3/1992 | Lanier et al. | 585/851 |
| 5,284,988 A * | 2/1994 | Schaerl et al. | 585/525 |
| 5,817,899 A * | 10/1998 | Hope et al. | 585/16 |
| 6,066,604 A | 5/2000 | Kaneko | |
| 2002/0147119 A1 | 10/2002 | Shimzu et al. | |
| 2002/0177744 A1 * | 11/2002 | Small et al. | 585/16 |

FOREIGN PATENT DOCUMENTS

| | | |
|---|---|---|
| JP | 63-51340 | 3/1988 |
| JP | 4-224893 | 8/1992 |
| JP | 6504786 | 6/1994 |
| JP | 7-133234 | 5/1995 |
| JP | 11-131081 | 5/1999 |
| JP | 2002-146377 | 5/2002 |
| JP | 2002-295487 | 10/2002 |
| JP | 2002-532328 | 10/2004 |
| WO | WO 96/41782 | 12/1996 |
| WO | WO 97/18278 | 5/1997 |
| WO | WO99/67347 | 12/1999 |
| WO | WO 02/092729 | 11/2002 |

* cited by examiner

PROCESS FOR PRODUCING SATURATED ALIPHATIC HYDROCARBON COMPOUND, AND LUBRICANT COMPOSITION

CROSS-REFERENCE TO RELATED APPLICATIONS

The present application is a continuation of PCT/JP2006/308890, filed on Apr. 27, 2006, and which claims priority to JP 2005-346533, filed on Nov. 30, 2005, and JP 2005-140220, filed on May 12, 2005, all of which are incorporated herein by reference.

TECHNICAL FIELD

The present invention relates to a process for producing a saturated aliphatic hydrocarbon compound and to a lubricant composition. Specifically, the present invention relates to a process for producing a saturated aliphatic hydrocarbon compound to be used in a base oil of lubricant having excellent low-temperature fluidity, low evaporativity, and thermal stability and oxidation stability, and to a lubricant composition containing the hydrocarbon compound.

BACKGROUND ART

In late years, lubricants have been required to have fuel-saving characteristics and energy-saving characteristics from the view point of global environmental protection, and also long-drain characteristics from the view point of resource saving. Because of this situation, low-viscosity, thermal resistance, and evaporation resistance will be the challenges of lubricants in the future. Therefore lubricants, which are excellent in thermal stability and oxidation stability, evaporation resistance, and low-temperature fluidity, have been demanded.

In general, any of lubricants may cause a deleterious change in low-temperature startup and a decrease in power efficiency when the viscosity of base oil is too high. On the contrary, if the viscosity is too low, an increase in oil consumption and a bearing damage due to insufficient lubricity may occur. Further, the flow-point, which represents an index of the low-temperature fluidity of the base oil, is preferably −20° C. or less, but not particularly limited to.

In view of improvement of the thermal stability and oxidation stability, synthetic lubricants are preferable. Examples of base oil known in the art include poly-α-olefins, α-olefin copolymers, polybutenes, alkylbenzenes, polyol esters, dibasic acid esters, polyoxyalkylene glycols, polyoxyalkylene glycol esters, polyoxyalkylene glycol ethers, and silicone oils.

The synthetic lubricant has both good points and bad points depending on intended purposes. In many cases, poly-α-olefin is used in consideration of thermal stability and oxidation stability as well as low viscosity. However, the conventional poly α-olefins include many isomers even in the saturated aliphatic hydrocarbon compounds having the same molecular weight, so any particular component (isomer) cannot be taken out by any purification process such as distillation. Thus, even a synthetic oil with a certain viscosity becomes a mixture of a high-volatility component and a low-volatility component. When such a saturated aliphatic hydrocarbon compound is used as a lubricant, the high-volatility component will vaporize at first to cause an increase in viscosity of the lubricant in a machine at work. Therefore, the conventional poly-α-olefins cause frequent repetition of oil change before the maintenance time. The lubricant may be ideally configured to provide oil that allows a mechanical maintenance and a change of oil to be carried out at the same time or to provide oil that does not require any oil-change.

Further, with respect to compressor oils used in compression equipment and so on, in consideration of resource saving and non-pollution, rotary air compressors have been widely used because of their high efficiencies, small oscillations, and small noises, in place of the conventional reciprocating air compressors. The lubricating condition of the rotary air compressor, such as the contact of the lubricant with high-temperature and high-pressure air, is more stringent compared with the reciprocating type. In addition, the recent rotary air compressors have been downsized more than before, and their opportunities to be operated under bad ambient environment such as under oxidative gas (e.g., SOx or NOx) atmosphere or cutting-oil mist atmosphere have been increased. In such cases, sludge arises in the oil. The sludge attaches to the inside of the device and causes a filter blockage in an extremely short time, so the operation of the device may become impossible. Therefore, oil with a high sludge resistance under such an environment has been demanded.

As a process for improving the sludge resistance, in general, there are (1) a process of mixing a base oil having a high solubility of the generated sludge, such as alkylbenzene, alkyl naphthalene, or ester oil, with mineral oil; and (2) a process of adding a detergent-dispersant to mineral oil. However, as a process of most advantageously preventing the generation of sludge by the oxidation stability of base oil itself, a synthetic saturated aliphatic hydrocarbon compound has come to be used as the base oil of compressor oil in stead of mineral oil. In this case, the hydrogenation products of α-olefin oligomers using $BF_3$ catalyst are widely used now. However, this manufacturing process cannot control the molecular distribution of oligomer and generate a myriad of isomers of each of compounds having the same degree of polymerization. Therefore, the product obtained by oligomerization of α-olefin with $BF_3$ catalyst has a large amount of evaporation loss because of an extended boiling-point range with a difficulty in purification. Therefore, the development of a new synthetic oil, which can take the place of such poly-α-olefin has been demanded in the art.

With respect to vacuum-pump oil, as another example, vacuum technologies have been widely used in the fields of semiconductor production, solar cells, aircrafts, automobiles, and opto-electronics. In order to implement these technologies, conventionally, mechanical vacuum pumps such as a reciprocating vacuum pump and a rotary vacuum pump, and high vacuum pumps such as a rotary oil vacuum pump and an oil vacuum diffusion pump, have been widely known in the art. Further, a vacuum-pump oil based on synthetic oil has been used for lubricating, highly vacuating, and prolonging the life of movable parts of these vacuum pumps.

In late years, in association with the expansion of applicable field of the vacuum pump, thermal stability and an extensive degree of vacuum have been demanded and an improvement of vacuum-pump oil to satisfy such demands has been conducted. Further, in the field of application of the vacuum technology, the shortening of time leading to stable operation after activation of a vacuum pump has been demanded for productivity improvement. However, a vacuum-pump oil based on a saturated aliphatic hydrocarbon shows, in particular, poor low-temperature starting characteristics when used during the winter season or on cold district. In other words, such a vacuum pump requires a long time before leading to the stable operation. As a result, there are problems of a decrease in productivity of a target product and a difficulty in obtaining the stable quality of the product.

Therefore, the development of novel synthetic oil has been demanded, in which the novel synthetic oil will have fluidity at low temperature and good thermal stability, and is capable of securing a high degree of vacuum and taking the place of the conventionally-used poly-α-olefin.

Further, rotational speeds of spindle motors used in electrical machineries and apparatuses, in particular, CD, DVD, HDD, polygon scanner, and the like have been increased year by year. At present, a high-rotational speed of 10,000 rpm or more is demanded. Conventionally, a rolling bearing typified by a ball-bearing has been used in each of these spindle motors. However, noncontact dynamic pressure fluid dynamic bearing or oil-impregnated sintered bearing have come to be used in terms of performance and cost effectiveness. The performances (mainly running torques) of these fluid dynamic bearing and oil-impregnated sintered bearing at high-speed revolution may be often defined based on the viscosity of lubricant to be used. The running torque at the high-speed revolution tends to lower as the viscosity decreases.

These lubricants should be prevented from undergoing the evaporative loss or destructive loss as far as possible because lubricity should be kept throughout the life without refilling, when these lubricants are once enclosed in a bearing mechanism.

The evaporative loss of hydrocarbon base oil typified by the general mineral oil increases as the viscosity (molecular weight) thereof decreases. Thus, both lowering the viscosity and lowering the evaporativity are hardly attained at the same time. In addition, aiming at this coexistence, the technology using ester, which is a polar compound, in a base oil has been known in the art.

However, for example, when a polar substance such as ester is used, disadvantages may occur such that various resin materials, for example, coating materials such as CD and DVD discs and a structural material such as a motor frame, are deformed or changed in color. In particular, in the case of each of CD and DVD that perform recording with optical signals, a coating resin should be prevented from optically clouding or deforming as far as possible.

In view of the above, there is an environment in that an ester-based oil solution having excellent characteristics cannot be substantially used. In contrast, in the case of CD and DVD discs and motor equipment using large amounts of resin materials, a lubricant using poly-α-olefin, which has lower evaporativities compared with that of mineral oil and excellent thermal resistance, has been conventionally used as a base oil.

The poly-α-olefin, which has been often used, is one obtained by cationic polymerization with $BF_3$ catalyst to oligomerize α-olefin and then hydrogenation thereof. However, this method cannot control the molecular distribution of oligomer and many different isomers even from the respective compounds having the same degree of polymerization are generated. Therefore, the product obtained by oligomerization of α-olefin with $BF_3$ catalyst has an extended boiling-point range with a difficulty in purification, so there is a disadvantage of a lot of evaporation loss.

As a process for manufacturing poly-α-olefin, a process for dimerizing a linear α-olefin using a Ziegler (organic aluminum compound) catalyst and then dimerizing a dimer using a Friedel craft catalyst is known (Patent Document 1).

The Ziegler catalyst of this Patent Document 1 leads to a low yield of a dimer even if a long-chain α-olefin is oligomerized, Therefore, an organic aluminum compound, which is a kind of the Ziegler catalyst, may be employed as dimerization catalyst. In this case, however, the content of vinyliden olefin in the dimer is low even though the dimerization of the organic aluminum compound advances. Thus, there is a disadvantage in that the dimer will lead to a low content of α-olefin tetramer even though it is subjected to dimerization and hydrogenation.

For the oligomerization of decene, acid catalyst (such as $BF_3$) has been currently used and a decene trimer hydride with a low flash point has been produced while having a high viscosity (Patent Document 2). In addition, in late years, a dewaxing lubricant obtained by oligomerizing decenes has been introduced. However, even if kinematic viscosities can be coincident with each other, any lubricant having low-temperature fluidity with high flash point cannot be obtained in the same kinematic viscosity (Patent Document 3).

In addition, as a process for producing a decene oligomer, there is known that a decene oligomer having a number average molecular weight of 500 to 200,000 is produced using a metallocene catalyst, subsequently hydrogenated as needed, and used as a lubricant base oil (Patent Document 4). In this process, for example, the oligomerization of $C_{10}$ (decene) leads to a decrease in a production ratio of $C_{20}$, $C_{30}$, and $C_{40}$ in this order, and a high yield of $C_{40}$ cannot be attained.

Patent Document 1: GB 961903 B
Patent Document 2: JP 10-504326 A
Patent Document 3: JP 2002-502436 A
Patent Document 4: JP 2002-518582 A

DISCLOSURE OF THE INVENTION

As described in the Background Art Section, instead of the saturated aliphatic hydrocarbon compound (poly-α-olefin) which has been conventionally used, the development of a novel synthetic lubricant having low-temperature fluidity and low evaporativity while having good thermal stability and good oxidation stability has been demanded.

An object of the present invention is to provide a lubricant composition containing a saturated aliphatic hydrocarbon compound having excellent oxidation stability, thermal stability, low evaporativity, and low-temperature fluidity, and a process for selectively producing such a saturated aliphatic hydrocarbon compound having these properties in high concentration.

As a result of intensive studies for solving the above-mentioned problems, the inventors of the present invention have found that a saturated aliphatic hydrocarbon compound having a predetermined structure in high concentration can be selectively produced by dimerizing an α-olefin in the presence of a metallocene complex catalyst to thereby obtain a vinylidene olefin, further dimerizing the vinylidene olefin in the presence of an acid catalyst, and hydrogenating the obtained dimer, or alternatively adding an α-olefin having a certain number of carbon atoms to the vinylidene olefin and subsequently hydrogenating the adduct. As a result, by using a lubricant including the saturated aliphatic hydrocarbon compound having a predetermined structure in high concentration a lubricant having excellent thermal stability, oxidation stability, low-temperature fluidity, and evaporative resistance can be obtained, thereby completing the present invention.

In other words, the present invention provides the following process for producing a saturated aliphatic hydrocarbon compound and a lubricant composition containing the saturated aliphatic hydrocarbon compound obtained by the process, a bearing oil, a bearing, and gyral equipment:

(1) a process for producing a saturated aliphatic hydrocarbon compound prepared using an α-olefin as a raw material and represented by the general formula (1):

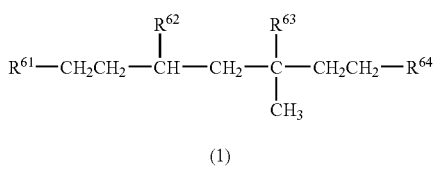

(1)

where $R^{61}$ to $R^{64}$ each represent independently a hydrogen atom or a liner or branched alkyl group having 1 to 16 carbon atoms, and a total number of carbon atoms in $R^{61}$ to $R^{64}$ is an integer of 4 to 64, including the steps of:

(I) producing a vinylidene olefin by dimerizing the α-olefin in a presence of a metallocene complex catalyst;

(II) further dimerizing the vinylidene olefin in a presence of an acid catalyst; and (III) hydrogenating a dimer obtained by the step (II);

(2) the process for producing a saturated aliphatic hydrocarbon compound according to Item (1), including a linear α-olefin as a raw material and producing a saturated aliphatic hydrocarbon compound represented by the general formula (1-a):

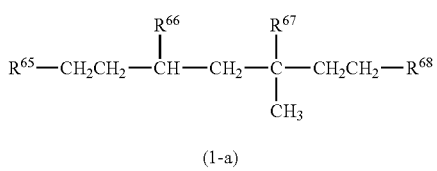

(1-a)

where $R^{65}$ to $R^{68}$ each represent independently a linear alkyl group having 8 to 16 carbon atoms);

(3) the process for producing a saturated aliphatic hydrocarbon compound according to Item (2), in which the linear α-olefin provided as the raw material is at least one olefin selected from the group consisting of 1-decene, 1-dodecene, and 1-tetradecene;

(4) the process for producing a saturated aliphatic hydrocarbon compound, according to any one of Items (1) to (3), in which the metallocene complex catalyst used in the step (I) contains:

a transition metal complex having a ligand having a conjugated five-membered carbon ring;

a compound composed of a cation and an anion in which multiple groups connect with elements; and/or an organic aluminum compound;

(5) the process for producing a saturated aliphatic hydrocarbon compound according to any one of Items (1) to (4), in which the acid catalyst used in the step (II) is a solid acid;

(6) a process for producing a saturated aliphatic hydrocarbon compound prepared using an α-olefin as a raw material and represented by the general formula (2):

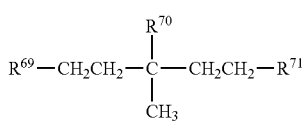

(2)

where $R^{69}$ represent a liner or branched alkyl group having 4 to 6-carbon atoms, $R^{70}$ and $R^{71}$ each represent independently a hydrogen atom or a liner or branched alkyl group having 1 to 16 carbon atoms, and a total number of carbon atoms in $R^{69}$ to $R^{71}$ is 3 to 48, including the steps of:

(IV) producing a vinylidene olefin by dimerizing an α-olefin in a presence of a metallocene complex catalyst;

(V) adding an α-olefin having 6 to 9 carbon atoms to the vinylidene olefin in a presence of an acid catalyst; and (VI) hydrogenating an α-olefin adduct obtained by the step (V);

(7) the process for producing a saturated aliphatic hydrocarbon compound according to Item (6), in which the metallocene complex catalyst used in the step (IV) contains:

a transition metal complex having a ligand having a conjugated five-membered carbon ring;

a compound composed of a cation and an anion in which multiple groups connect with elements; and/or an organic aluminum compound, (8) the process for producing a saturated aliphatic hydrocarbon compound according to Item (6) or (7), in which the acid catalyst used in the step (V) is a solid acid;

(9) a lubricant composition including:

a saturated aliphatic hydrocarbon compound according to any one of Items (1) to (5), represented by the general formula (1):

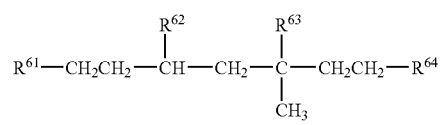

(1)

where $R^{61}$ to $R^{64}$ each represent independently a hydrogen atom or a liner or branched alkyl group having 1 to 16 carbon atoms, and the total number of carbon atoms in $R^{61}$ to $R^{64}$ is an integer of 4 to 64; and/or a saturated aliphatic hydrocarbon compound according to any one of Items (6) to (8), represented by the general formula (2):

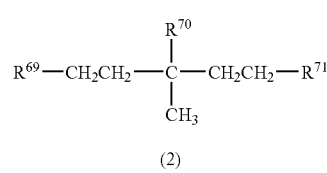

(2)

where $R^{69}$ is a linear or branched alkyl group having 4 to 6 carbon atoms, $R^{70}$ and $R^{71}$ each represent independently a hydrogen atom or a liner or branched alkyl group having 1 to 16 carbon atoms, and the total number of carbon atoms in $R^{69}$ to $R^{71}$ is an integer of 3 to 48;

(10) the lubricant composition according to Item (9), in which the saturated aliphatic hydrocarbon compound is a compound represented by the general formula (1-a);

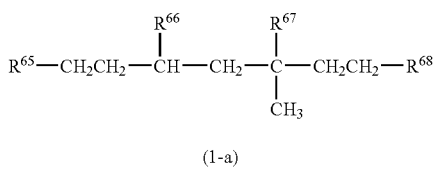

(1-a)

where $R^{65}$ to $R^{68}$ each represent independently a linear alkyl group having 8 to 16 carbon atoms;

(11) the lubricant composition according to Item (10), in which $R^{65}$ to $R^{68}$ in the general the formula (1-a) each represent a linear alkyl group having 8 to 12 carbon atoms;

(12) the lubricant composition according to Item (11), in which:

the linear α-olefin provided as the raw material is 1-decene; and the saturated aliphatic hydrocarbon compound contains 11-methyl-11,13-dioctyl tricosane in an amount of 55% by mass or more;

(13) the lubricant composition according to Item (12), in which:

the linear α-olefin provided as the raw material is 1-decene; and a content of 11-methyl-11,13-dioctyl tricosane occupied in the saturated aliphatic hydrocarbon compound having 40 carbon atoms is 65% by mass or more;

(14) the lubricant composition according to any one of Items (9) to (13), further including:

at least one selected from an antioxidant, an oiliness agent, an extreme pressure agent, a detergent-dispersant, a viscosity index improver, a rust preventing agent, a metal deactivator, and a defoaming agent;

(15) the lubricant composition according to any one of Items (9) to (14) which is used in a hydraulic pressure, turbine, working machine, bearing, gear, or metal-working;

(16) a bearing oil including the lubricant oil composition according to any one of Items (9) to (15);

(17) a bearing including:

the bearing oil according to Item (16);

(18) the bearing according to Item (17), further including a dynamic pressure fluid dynamic bearing, an oil-containing bearing, or an oil-containing bearing provided with a dynamic pressure groove; and

(19) a gyral equipment including:

a bearing unit including a bearing according to Item (17) or (18).

DESCRIPTION OF SYMBOLS

Figure 1:
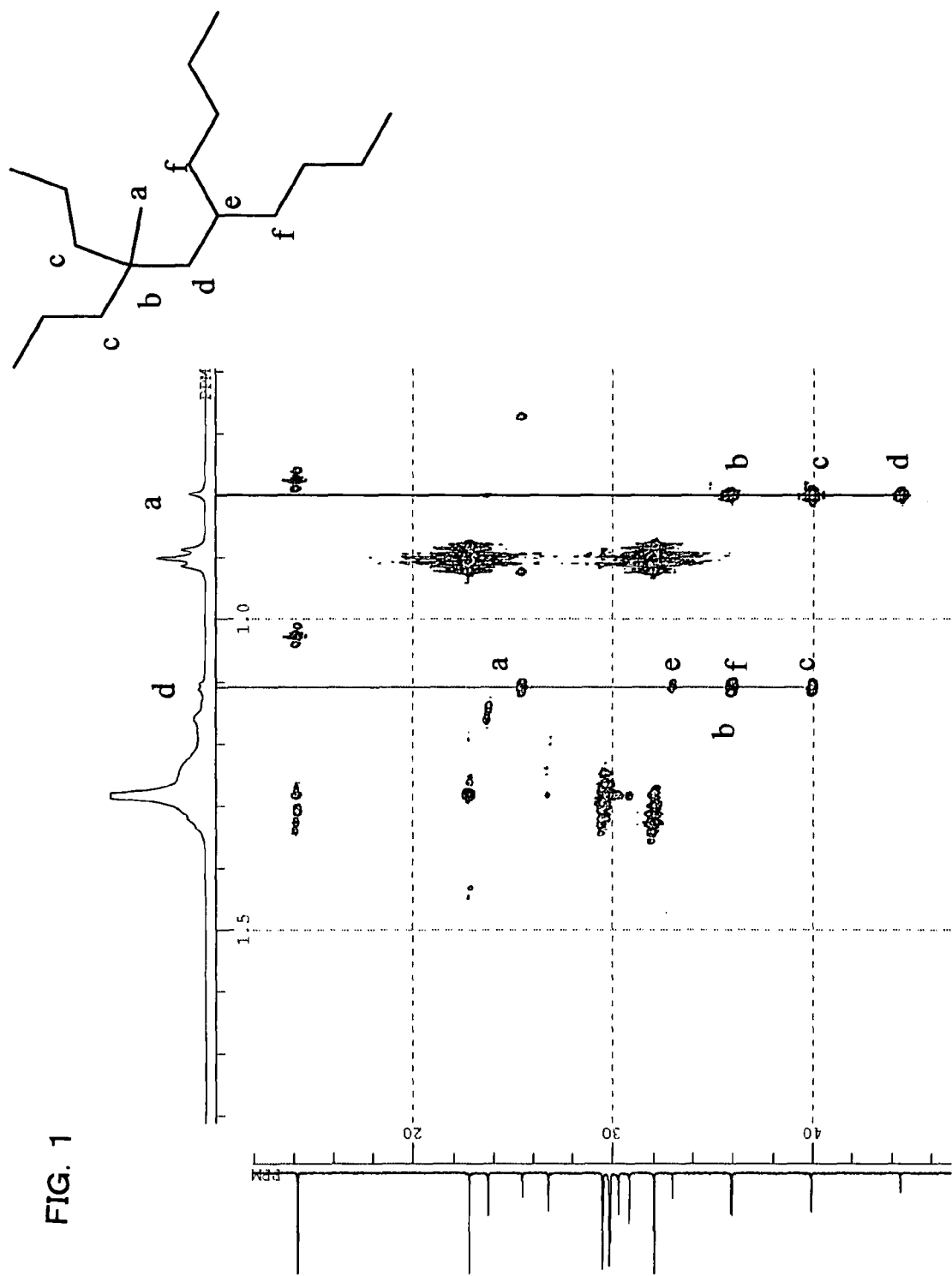
FIG. 1 is an analytical profile obtained by carrying out a long-range correlated analysis of 11-methyl-11,13-dioctyl tricosane, which was isolated in Example 1, with $C^{13}$-NMR.
Figure 2:
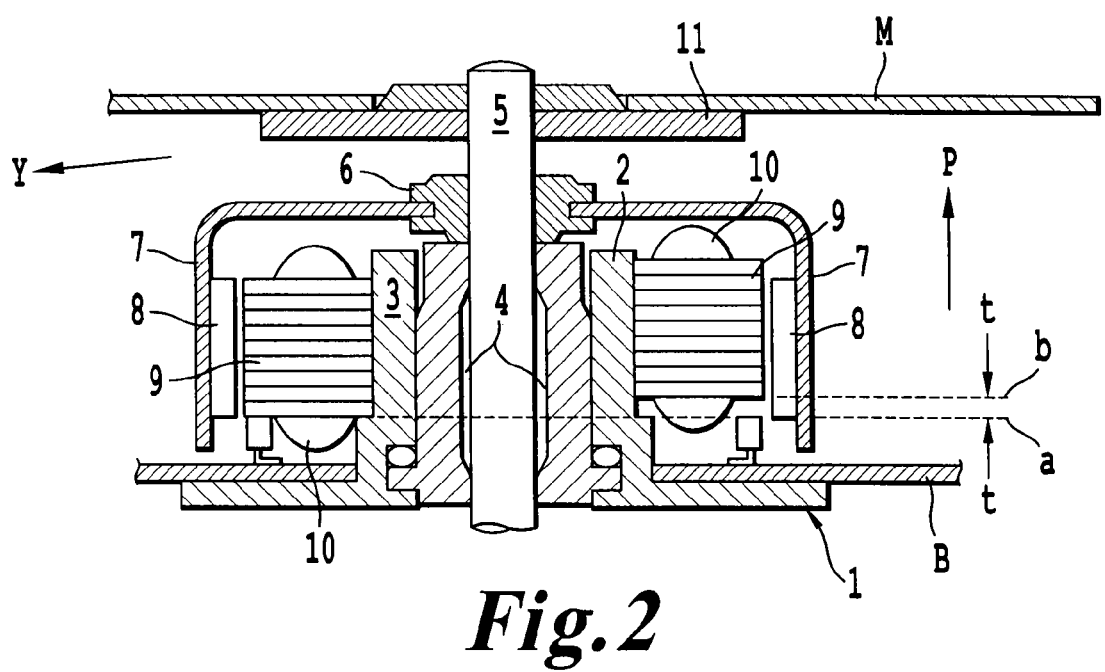
FIG. 2 is an enlarged cross-sectional diagram that illustrates an example of a spindle motor to which a lubricant composition of the present invention is applied.

| 1: | housing holder |
| 2: | cylindrical part |
| 3: | bearing |
| 4: | inner clearance part |
| 5: | motor axis |
| 6: | supporting member |
| 7: | rotor |
| 8: | magnet |
| 9: | laminated core |
| 10: | coil |
| 11: | turn table |
| B: | base plate |
| M: | rotation medium |

BEST MODE FOR CARRYING OUT THE INVENTION

At first, a process for producing a saturated aliphatic hydrocarbon compound including a high concentration of the saturated aliphatic hydrocarbon compound represented by the general formula (1) will be described:

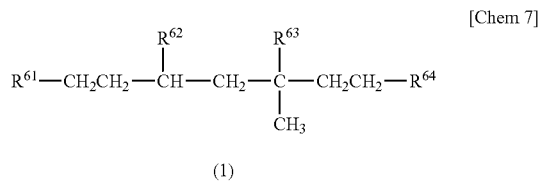

(1)

where $R^{61}$ to $R^{64}$ each represent independently a hydrogen atom or a liner or branched alkyl group having 1 to 16 carbon atoms, and the total number of carbon atoms in $R^{61}$ to $R^{64}$ is an integer of 4 to 64.

The inventors of the present invention have found that, as a process for selectively producing a certain component from among saturated aliphatic hydrocarbon compounds expected to have oxidation stabilities, an α-olefin is dimerized in the presence of a metallocene catalyst at first, the obtained vinylidene olefin is further dimerized and then hydrogenated to obtain the saturated aliphatic hydrocarbon compound represented by the above general formula (1) (Compound 1) in high concentration, i.e., to obtain a compound having a certain structure in saturated aliphatic hydrocarbon compounds having the same molecular weight in high concentration.

In other words, in order to increase the content of Compound 1, a vinyl olefin (Compound 3) represented by the general formula (3) as described below is produced as the dimer of α-olefin (intermediate product) and then dimerized, followed by hydrogenation:

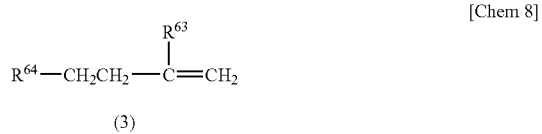

(3)

where $R^{63}$ to $R^{64}$ are respectively identical with those mentioned above.

In order to produce the vinylidene olefin in high concentration in the dimer, the present invention uses a metallocene complex catalyst, while in Patent Document 1a Ziegler catalyst is used. Thus, the production ratio of vinylidene olefin in the dimer increases and the dimer is then further dimerized to produce a tetramer having an extensively increased ratio of the general formula (4) or (5) as described below. Further, for practical usage, the compound of the following general formula (4) or (5) is hydrogenated to secure oxidation stability and thermal stability, thereby obtaining a saturated aliphatic hydrocarbon compound represented by the general formula (1) as described above:

[Chem 9]

$$R^{61}-CH_2CH_2-\underset{\underset{CH_3}{|}}{\overset{R^{62}}{C}}=CH-\underset{\underset{CH_3}{|}}{\overset{R^{63}}{C}}-CH_2CH_2-R^{64} \quad (4)$$

$$R^{61}-CH_2CH=\underset{}{\overset{R^{62}}{C}}-CH_2-\underset{\underset{CH_3}{|}}{\overset{R^{63}}{C}}-CH_2CH_2-R^{64} \quad (5)$$

where $R^{61}$ to $R^{64}$ are respectively identical with those mentioned above.

Therefore, the reaction steps of the process for producing the saturated aliphatic hydrocarbon compound of the present invention are the following three steps:

(I) Step of Producing a Vinylidene Olefin:

Dimerization of an α-olefin in the presence of a metallocene complex catalyst.

(II) Step of Dimerizing the Vinylidene Olefin:

Dimerization of the vinylidene olefin in the presence of an acid catalyst.

(III) Step of Hydrogenating the Vinylidene Olefin Dimer:

Gas-phase hydrogenation of the vinylidene olefin dimer in the presence of a hydrogenation catalyst.

In the present invention, in the saturated aliphatic hydrocarbon compound represented by the general formula (1) obtained as described above, in which a liner α-olefin is used as an α-olefin raw material and each of $R^{61}$ to $R^{64}$ is a linear alkyl group having 8 to 26 carbon atoms, the saturated aliphatic hydrocarbon compound represented by the following general formula (1-a) (Compound 1-a) is preferable in terms of performance:

[Chem 10]

$$R^{65}-CH_2CH_2-\overset{R^{66}}{\underset{|}{CH}}-CH_2-\underset{\underset{CH_3}{|}}{\overset{R^{67}}{C}}-CH_2CH_2-R^{68} \quad (1\text{-a})$$

where $R^{65}$ to $R^{68}$ each represent independently a linear alkyl group having 8 to 16 carbon atoms.

(I) Step of Producing Vinylidene Olefin:

In this step, an α-olefin is dimerized by carrying out the reaction under predetermined conditions in the presence of a metallocene complex catalyst, so the vinylidene olefin represented by the above general formula (3) can be selectively obtained in high yield.

In general formulae (1) and (3) to (5), $R^{61}$ to $R^{64}$ each represent independently a hydrogen atom or a linear or branched alkyl group having 1 to 16 carbon atoms. In the present invention, however, a linear alkyl group having 8 to 16 carbon atoms as described above is preferable. In other words, Compound 1-a is preferable among the members of Compound 1. Examples of the linear alkyl group having 8 to 16 carbon atoms include an n-octyl group, an n-nonyl group, an n-decyl group, n-undecyl group, an n-dodecyl group, an n-tridecyl group, an n-tetra decyl group, an n-pentadecyl group, and an n-hexadecyl group.

Therefore, the raw material of α-olefin is preferably a linear α-olefin represented by the general formula:

$$H_2C=CH-(CH_2)_n-CH_3$$

where n represents an integer of 7 to 15, for example, including 1-decene, 1-dodecen, 1-tridecene, 1-tetradecene, 1-pentadecene, 1-hexadecene, 1-heptadecene, and 1-octadecene. Of those, 1-decene, 1-dodecen, and 1-tetradecene, which are α-olefins with n of 7, 9, and 11, are preferable. These α-olefins may be used a single kind thereof or may be used two or more kinds thereof in combination.

The metallocene complex catalyst to be generally used may be a catalyst containing at least one selected from (i) a metallocene complex including a ligand having a conjugated five-membered carbon ring and a transition metal of the Group 4 to Group 6 in the periodic table; (ii) (ii-1) a compound composed of a cation and an anion in which plural groups connect with elements; and (ii-2) an organic aluminum compound.

A preferable transition metal compound is one (i) containing a ligand having a conjugated five-membered carbon ring and the metallocene complex of the Group 4 to Group 6 in the periodic table may be preferably a transition metal compound represented by the general formula (III) or the general formula (IV) in terms of activity.

$$Q^1{}_a(C_5H_{5-a-b}R^1{}_b)(C_6H_{5-a-c}R^2{}_c)M^1X_eY_f \quad (III)$$

$$Q^2{}_a(C_5H_{5-a-d}R^3{}_d)ZM^1X_eY_f \quad (IV)$$

In the formulae, $Q^1$ represents a connective group cross-linking two conjugated five-membered ring ligands: $(C_5H_{5-a-b}R^1{}_b)$ and $(C_6H_{5-a-c}R^2{}_c)$ and $Q^2$ represents a connective group cross-linking a conjugated five-membered ring ligand $(C_5H_{5-a-d}R^3{}_d)$ and a Z group. (e+f) represents (the value subtracting 2 from the valence of $M^1$). $M^1$ represents a transition metal of the Group 4 to Group 6 in the periodic table. X, Y, and Z each represent independently a covalently-binding and an ion-binding ligand.

Specific examples of $Q_1$ and $Q_2$ include: (1) an alkylene group having 1 to 4 carbon atoms, a cycloalkylene group, or a side-chain lower alkylene or phenyl substituent thereof, such as a methylene group, an ethylene group, an isopropylene group, a methylphenyl methylene group, a diphenyl methylene group, or a cyclohexylene group, (2) a silylene group, an oligosilylene group, or a side-chain lower molecule alkylene or phenyl substituent thereof, such as a silylene group, a dimethyl silylene group, a methylphenyl silylene group, a diphenyl silylene group, a disilylene group, or a tetramethyl disilylene group, and (3) a hydrocarbon group containing germanium, phosphorus, nitrogen, boron, or aluminum (such as lower alkyl group, phenyl group, hydrocarbyl oxy group (preferably lower alkoxy group)), such as a $(CH_3)_2$ Ge group, a $(C_6H_5)_2$ Ge group, a $(CH_3)$ P group, a $(C_6H_5)$ P group, a $(C_4H_9)$ N group, a $(C_6H_5)$ N group, a $(CH_3)$ B group, a $(C_4H_9)$ B group, a $(C_6H_5)$ B group, a $(C_6H_5)$ Al group, or a $(CH_3O)$ Al group. Of those, the alkylene group and the silylene group are preferable in term of activity.

In addition, $(C_5H_{5-a-b}R^1{}_b)$, $(C_5H_{5-a-c}R^2{}_c)$, and $(C_5H_{5-a-d}R^3{}_d)$ are conjugated five-membered ring ligands, in which $R^1$, $R^2$, and $R^3$ each represent a hydrocarbon group, a halogen atom, an alkoxy group, a silicon-containing hydrocarbon group, a phosphorus-containing hydrocarbon group, a nitrogen-containing hydrocarbon group, or a boron-containing hydrocarbon group. In addition, a is 0, 1, or 2. Further, each of b, c, and d represents an integer of 0 to 5 when a=0, an integer of 0 to 4 when a=1, and an integer of 0 to 3 when a=2. Herein, the hydrocarbon group is preferably one having 1 to 12 carbon atoms, particularly 1 to 12 carbon atoms. The hydrocarbon group may be a monovalent group and may bind to a conjugated five-membered ring such as a cyclopentadienyl group. Alternatively, if a plurality of, hydrocarbon groups is present, two of them may be connected to each other to form a ring structure together with part of the cyclopentdienyl group.

A representative example of the conjugated five-membered group is a substituted or unsubstituted cyclopentdenyl group, an indenyl group, and a fluorenyl group. The halogen atoms include chlorine, bromine, iodine, and fluorine atoms, while the alkoxy group include preferably those having 1 to 20 carbon atoms. The silicon-containing hydrocarbon group may be, for example, —Si $(R^4)(R^5)(R^6)$ ($R^4$, $R^5$, and $R^6$ are hydrocarbon groups having 1 to 24 carbon atoms, respectively). The phosphorus-containing hydrocarbon group, the nitrogen-containing hydrocarbon group, and the boron-containing hydrocarbon group may be —$P(R^7)(R^8)$, —$N(R^7)(R^8)$, and —$B(R^7)(R^8)$ ($R^7$ and $R^8$ are hydrocarbon groups having 1 to 18 carbon atoms, respectively), respectively.

If each of $R^1$, $R^2$, and $R^3$ is present in plural, the plural R's, the plural $R^2$s, and the plural $R^3$s may be identical with one another or may be different from one another. In addition, in the general formula (III), the conjugated five-membered ring ligands, $(C_5H_{5-a-b}R^1_b)$ and $(C_5H_{5-a-c}R^2_c)$ may be identical with each other or may be different from each other.

The hydrocarbon groups having 1 to 24 carbon atoms and the hydrocarbon groups having 1 to 18 carbon atoms include alkyl groups, alkenyl groups, aryl groups, and alicyclic aliphatic hydrocarbon groups. The alkyl groups include a methyl group, an ethyl group, an n-propyl group, an isopropyl group, an n-butyl group, an isobutyl group, a tert-butyl group, an n-hexyl group, and an n-decyl group, and those having 1 to 20 carbon atoms are preferable. The alkenyl groups include a vinyl group, a 1-propenyl group, a 1-butenyl group, a 1-hexenyl group, an 1-octenyl group, and a cyclohexenyl group, and those having 2 to 10 carbon atoms are preferable in the present invention. The aryl groups include a phenyl group, a tolyl group, a xylyl group, and a naphthyl group, and in the present invention those having 6 to 14 carbon atoms are preferable. The alicyclic aliphatic hydrocarbon groups include a cyclopropyl group, a cyclopentyl group, and a cyclohexyl group.

On the other hand, $M^1$ represents any of transition metals of the Group 4 to Group 6 in the periodic table and specific examples thereof include titanium, zirconium, hafnium, vanadium, niobium, molybdenum, and tungsten. Of those, titanium, zirconium, and hafnium are preferable in terms of activity. Z is a covalently-binding ligand and specific examples thereof include halogen atoms, oxygen (—O—), sulfur (—S—), alkoxy groups having 1 to 20 carbon atoms, preferably 1 to 10 carbon atoms, thioalkoxy groups having 1 to 20 carbon atoms, preferably 1 to 12 carbon atoms, nitrogen-containing hydrocarbon groups having 1 to 40 carbon atoms, preferably 1 to 18 carbon atoms (for example, t-butyl amino group and t-butyl imino group), and phosphorus-containing hydrocarbon groups having 1 to 40 carbon atoms, preferably 1 to 18 carbon atoms. X and Y each represent a covalently-binding ligand or a binding ligand, specifically a hydrogen atom, a halogen atom, a hydrocarbon group having 1 to 20 carbon atoms, preferably 1 to 10 carbon atoms, an alkoxy group having 1 to 20 carbon atoms, preferably 1 to 10 carbon atoms, an amino group, a phosphorus-containing hydrocarbon group having 1 to 20 carbon atoms, preferably 1 to 12 carbon atoms (for example, diphenyl phosphine group), or a silicon-containing hydrocarbon group having 1 to 20 carbon atoms, preferably 1 to 12 carbon atoms (for example, trimethyl silyl group), a hydrocarbon group having 1 to 20 carbon atoms, preferably 1 to 12 carbon atoms, or a halogen-containing boron compound (for example, $B(C_6H_5)_4$ or $BF_4$). Of those, the halogen atom and the hydrocarbon group are preferable. The X and the Y may be identical with each other or may be different from each other. Among the transition metal compounds represented by the general formula (6) or (7), a complex having a ligand with an indenyl, cyclopentane dienyl or fluorenyl structure is particularly preferable.

Specific examples of the transition metal compound represented by the above general formula (III) or (IV) include the following compounds:

(a) Transition-metal compounds not having a crosslinkable bonding group but having two conjugated five-membered ligands, such as bis(cyclopentadienyl)titanium dichloride, bis(methylcyclopentadienyl)titanium dichloride, bis(dimethylcyclopentadienyl)titanium dichloride, bis(trimethylcyclopentadienyl)titanium dichloride, bis(tetramethylcyclopentadienyl)titanium dichloride, bis(pentamethylcyclopentadienyl)titanium dichloride, bis(n-butylcyclopentadienyl)titanium dichloride, bis(indenyl)titanium dichloride, bis(fluorenyl)titanium dichloride, bis(cyclopentadienyl)titanium chlorohydride, bis(cyclopentadienyl)methyltitanium chloride, bis(cyclopentadienyl)ethyltitanium chloride, bis(cyclopentadienyl)phenyltitanium chloride, bis(cyclopentadienyl)dimethyltitanium, bis(cyclopentadienyl)diphenyltitanium, bis(cyclopentadienyl)dineopentyltitanium, bis(cyclopentadienyl)dihydrotitanium, (cyclopentadienyl)(indenyl)titanium dichloride, (cyclopentadienyl)(fluorenyl)titanium dichloride, bis(cyclopentadienyl)zirconium dichloride, bis(methylcyclopentadienyl)zirconium dichloride, bis(dimethylcyclopentadienyl)zirconium dichloride, bis(trimethylcyclopentadienyl)zirconium dichloride, bis(tetramethylcyclopentadienyl)zirconium dichloride, bis(pentamethylcyclopentadienyl)zirconium dichloride, bis(n-butylcyclopentadienyl)zirconium dichloride, bis(indenyl)zirconium dichloride, bis(fluorenyl)zirconium dichloride, bis(cyclopentadienyl)zirconium chlorohydride, bis(cyclopentadienyl)methylzirconium chloride, bis(cyclopentadienyl)ethylzirconium chloride, bis(cyclopentadienyl)phenylzirconium chloride, bis(cyclopentadienyl)dimethylzirconium, bis(cyclopentadienyl)diphenylzirconium, bis(cyclopentadienyl)dineopentylzirconium, bis(cyclopentadienyl)dihydrozirconium, (cyclopentadienyl)(indenyl)zirconium dichloride, and (cyclopentadienyl)(fluorenyl)zirconium dichloride.

(b) Transition-metal compounds having two alkylene-crosslinked, conjugated five-membered cyclic ligands, such as methylenebis(indenyl)titanium dichloride, ethylenebis(indenyl)titanium dichloride, methylenebis(indenyl)titanium chlorohydride, ethylenebis(indenyl)methyltitanium chloride, ethylenebis(indenyl)methoxychlorotitanium, ethylenebis(indenyl)titanium diethoxide, ethylenebis(indenyl)dimethyltitanium, ethylenebis(4,5,6,7-tetrahydroindenyl)titanium dichloride, ethylenebis(2-methylindenyl)titanium dichloride, ethylenebis(2,4-dimethylindenyl)titanium dichloride, ethylenebis(2-methyl-4-trimethylsilylindenyl)titanium dichloride, ethylenebis(2,4-dimethyl-5,6,7-trihydroindenyl) titanium dichloride, ethylene(2,4-dimethylcyclopentadienyl)(3',5'-dimethylcyclopentadienyl)titanium dichloride, ethylene(2-methyl-4-t-butylcyclopentadienyl)(3'-t-butyl-5'-methylcyclopentadienyl)titanium dichloride, ethylene(2,3,5-trimethylcyclopentadienyl)(2',4',5'-trimethylcyclopentadienyl) titanium dichloride, isopropylidene bis(2-methylindenyl)titanium dichloride, isopropylidene bis(indenyl)titanium dichloride, isopropylidene bis(2,4-dimethylindenyl)titanium dichloride, isopropylidene (2,4-dimethylcyclopentadienyl)(3',5'-dimethylcyclopentadienyl)titanium dichloride, isopropylidene (2-methyl-4-t-butylcyclopentadienyl)(3'-t-butyl-5'-methylcyclopentadienyl)titanium dichloride, methylene (cyclopentadienyl)(3,4-dimethylcyclopentadienyl)titanium dichloride, methylene(cyclopentadienyl)(3,4-dimethylcyclopentadienyl)titanium chlorohydride, methylene(cyclopentadienyl)(3,4-dimethylcyclopentadienyl)dimethyltitanium, methylene(cyclopentadienyl)(3,4-dimethylcyclopentadienyl)diphenyltitanium, methylene (cyclopentadienyl)(trimethylcyclopentadienyl)titanium dichloride, methylene(cyclopentadienyl)(tetramethylcyclopentadienyl)titanium dichloride, isopropylidene (cyclopentadienyl)(3,4-dimethylcyclopentadienyl)titanium dichloride, isopropylidene (cyclopentadienyl)(2,3,4,5-tetramethylcyclopentadienyl)titaniu m dichloride, isopropylidene (cyclopentadienyl)(3-methylindenyl)titanium dichloride, isopropylidene (cyclopentadienyl)(fluorenyl)titanium dichloride, isopropylidene (2-methylcyclopentadienyl)(fluorenyl)titanium dichloride, isopropylidene (2,5-dimethylcyclopentadienyl)(3,4-dimethylcyclopentadienyl)titanium dichloride, isopropylidene (2,5-dimethylcyclopentadienyl)(fluorenyl)titanium dichloride, ethylene(cyclopentadienyl)(3,5-dimethylcyclopentadienyl)titanium dichloride, ethylene(cyclopentadienyl)(fluorenyl)titanium dichloride, ethylene(2,5-dimethylcyclopentadienyl)(fluorenyl)titanium dichloride, ethylene(2,5-diethylcyclopentadienyl)(fluorenyl)titanium dichloride, diphenylmethylene(cyclopentadienyl)(3,4-diethylcyclopentadienyl)titanium dichloride, diphenylmethylene (cyclopentadienyl)(3,4-diethylcyclopentadienyl)titanium dichloride, cyclohexylidene (cyclopentadienyl)(fluorenyl)titanium dichloride, cyclohexylidene (2,5-dimethylcyclopentadienyl)(3',4'-dimethylcyclopentadienyl)titanium dichloride, methylenebis(indenyl)zirconium dichloride, ethylenebis(indenyl)zirconium dichloride, methylenebis(indenyl)zirconium chlorohydride, ethylenebis(indenyl)methylzirconium chloride, ethylenebis(indenyl)methoxychlorozirconium, ethylenebis(indenyl)zirconium diethoxide, ethylenebis(indenyl)dimethylzirconium, ethylenebis(4,5,6,7-tetrahydroindenyl)zirconium dichloride, ethylenebis(2-methylindenyl)zirconium dichloride, ethylenebis(2,4-dimethylindenyl)zirconium dichloride, ethylenebis(2-methyl-4-trimethylsilylindenyl)zirconium dichloride, ethylenebis(2,4-dimethyl-5,6,7-trihydroindenyl)zirconium dichloride, ethylene(2,4-dimethylcyclopentadienyl)(3',5'-dimethylcyclopentadienyl)zirconium dichloride, ethylenebis(2-methyl-4-t-butylcyclopentadienyl)(3'-t-butyl-5'-methylcyclopentadienyl)zirconium dichloride, ethylene(2,3,5-trimethylcyclopentadienyl)(2',4',5'-trimethylcyclopentadienyl)zirconium dichloride, isopropylidenebis(2-methylindenyl)zirconium dichloride, isopropylidenebis(indenyl)zirconium dichloride, isopropylidenebis(2,4-dimethylindenyl)zirconium dichloride, isopropylidene(2,4-dimethylcyclopentadienyl)(3',5'-dimethylcyclopentadienyl)zirconium dichloride, isopropylidene(2-methyl-4-t-butylcyclopentadienyl)(3'-t-butyl-5'-methylcyclopentadienyl)zirconium dichloride, methylene (cyclopentadienyl)(3,4-dimethylcyclopentadienyl) zirconium dichloride, methylene(cyclopentadienyl)(3,4-dimethylcyclopentadienyl)zirconium chlorohydride, methylene(cyclopentadienyl)(3,4-dimethylcyclopentadienyl)dimethylzirconium, methylene(cyclopentadienyl)(3,4-dimethylcyclopentadienyl)diphenylzirconium, methylene (cyclopentadienyl)(trimethylcyclopentadienyl)zirconium dichloride, methylene(cyclopentadienyl)(tetramethylcyclopentadienyl)zirconium dichloride, isopropylidene(cyclopentadienyl)(3,4-dimethylcyclopentadienyl)zirconium dichloride, isopropylidene(cyclopentadienyl)(2,3,4,5-tetramethylcyclopentadienyl)zirconium dichloride, isopropylidene(cyclopentadienyl)(3-methylindenyl)zirconium dichloride, isopropylidene(cyclopentadienyl)(fluorenyl)zirconium dichloride, isopropylidene(2-methylcyclopentadienyl)(fluorenyl)zirconium dichloride, isopropylidene (2,5-dimethylcyclopentadienyl)(3,4-dimethylcyclopentadienyl)zirconium dichloride, isopropylidene(2,5-dimethylcyclopentadienyl)(fluorenyl) zirconium dichloride, ethylene(cyclopentadienyl)(3,5-dimethylcyclopentadienyl)zirconium dichloride, ethylene (cyclopentadienyl)(fluorenyl)zirconium dichloride, ethylene(2,5-dimethylcyclopentadienyl)(fluorenyl)zirconium dichloride, ethylene(2,5-diethylcyclopentadienyl)(fluorenyl) zirconium dichloride, diphenylmethylene(cyclopentadienyl) (3,)hafnium diethoxide, ethylenebis(indenyl)(dimethylhafnium4-diethylcyclopentadienyl)zirconium dichloride, diphenylmethylene(cyclopentadienyl)(3,4-diethylcyclopentadienyl)zirconium dichloride, cyclohexylidene(cyclopentadienyl)(fluorenyl)zirconium dichloride, cyclohexylidene(2,5-dimethylcyclopentadienyl)(3',4'-dimethylcyclopentadienyl)zirconium dichloride, methylenebis(indenyl)hafnium dichloride, ethylenebis(indenyl)hafnium dichloride, methylenebis(indenyl)hafnium chlorohydride, ethylenebis(indenyl)methylhafnium chloride, ethylenebis(indenyl)methoxychlorohafnium, ethylenebis(indenyl)hafnium diethoxide, ethylenebis(indenyl)dimethylhafnium, ethylenebis(4,5,6,7-tetrahydroindenyl)hafnium dichloride, ethylenebis(2-methylindenyl)hafnium dichloride, ethylenebis(2,4-dimethylindenyl)hafnium dichloride, ethylenebis(2-methyl-4-trimethylsilylindenyl)hafnium dichloride, ethylenebis(2,4-dimethyl-5,6,7-trihydroindenyl) hafnium dichloride, ethylene(2,4-dimethylcyclopentadienyl) (3',5'-dimethylcyclopentadienyl)hafnium dichloride, ethylene(2-methyl-4-t-butylcyclopentadienyl)(3'-t-butyl-5'-methylcyclopentadienyl)hafnium dichloride, ethylene(2,3,5-trimethylcyclopentadienyl)(2',4',5'-trimethylcyclopentadienyl) hafnium dichloride, isopropylidenebis(2-methylindenyl) hafnium dichloride, isopropylidenebis(indenyl)hafnium dichloride, isopropylidenebis(2,4-dimethylindenyl)hafnium dichloride, isopropylidene (2,4-dimethylcyclopentadienyl) (3',5'-dimethylcyclopentadienyl)hafnium dichloride, isopropylidene (2-methyl-4-t-butylcyclopentadienyl)(3'-t-butyl-5'-methylcyclopentadienyl)hafnium dichloride, methylene (cyclopentadienyl)(3,4-dimethylcyclopentadienyl)hafnium dichloride, methylene(cyclopentadienyl)(3,4-dimethylcyclopentadienyl)hafnium chlorohydride methylene(cyclopentadienyl)(3,4-dimethylcyclopentadienyl)dimethylhafnium, methylene(cyclopentadienyl)(3,4-dimethylcyclopentadienyl)diphenylhafnium, methylene(cyclopentadienyl)(trimethylcyclopentadienyl)hafnium dichloride, methylene(cyclopentadienyl)(tetramethylcyclopentadienyl)hafnium dichloride, isopropylidene (cyclopentadienyl)(3,4-dimethylcyclopentadienyl)hafnium dichloride, isopropylidene (cyclopentadienyl)(2,3,4,5-tetramethylcyclopentadienyl)hafnium dichloride, isopropylidene (cyclopentadienyl)(3-methylindenyl)hafnium dichloride, isopropylidene (cyclopentadienyl) (fluorenyl)hafnium dichloride, isopropylidene (2-methylcyclopentadienyl)(fluorenyl)hafnium dichloride, isopropylidene (2,5-dimethylcyclopentadienyl)(3,4-dimethylcyclopentadienyl)hafnium dichloride, isopropylidene (2,5- dimethylcyclopentadienyl)(fluorenyl)hafnium dichloride, ethylene(cyclopentadienyl)(3,5-dimethylcyclopentadienyl)hafnium dichloride, ethylene(cyclopentadienyl)(fluorenyl)hafnium dichloride, ethylene(2,5-dimethylcyclopentadienyl)(fluorenyl)hafnium dichloride, ethylene(2,5-diethylcyclopentadienyl)(fluorenyl)hafnium dichloride, diphenylmethylene(cyclopentadienyl)(3,4-diethylcyclopentadienyl)hafnium dichloride, diphenylmethylene(cyclopentadienyl)(3,4-diethylcyclopentadienyl)hafnium dichloride, cyclohexylidene (cyclopentadienyl)(fluorenyl)hafnium dichloride, and cyclohexylidene (2,5-dimethylcyclopentadienyl)(3',4'-dimethylcyclopentadienyl)hafnium dichloride.

(c) Transition-metal compounds having two silylene-crosslinked, conjugated five-membered cyclic ligands, such as dimethylsilylenebis(indenyl)titanium dichloride, dimethylsilylenebis(4,5,6,7-tetrahydroindenyl)titanium dichloride, dimethylsilylenebis(2-methylindenyl)titanium dichloride, dimethylsilylenebis(2,4-dimethylindenyl)titanium dichloride, dimethylsilylenebis(2,4-dimethylcyclopentadienyl)(3',5'-dimethylcyclopentadienyl)titanium dichloride, dimethylsilylenebis(2-methyl-4,5-benzoindenyl)titanium dichloride, dimethylsilylenebis(2-methyl-4-naphtylindenyl)titanium dichloride, dimethylsilylenebis(2-methyl-4-phenylindenyl)titanium dichloride, phenylmethylsilylenebis(indenyl)titanium dichloride, phenylmethylsilylenebis(4,5,6,7-tetrahydroindenyl)titanium dichloride, phenylmethylsilylenebis(2,4-dimethylindenyl)titanium dichloride, phenylmethylsilylene(2,4-dimethylcyclopentadienyl)(3',5'-dimethylcyclopentadienyl)titanium dichloride, phenylmethylsilylene(2,3,5-trimethylcyclopentadienyl)(2',4',5'-trimethylcyclopentadienyl)titanium dichloride, phenylmethylsilylenebis(tetramethylcyclopentadienyl)titanium dichloride, diphenylsilylenebis(2,4-dimethylindenyl)titanium dichloride, diphenylsilylenebis(indenyl)titanium dichloride, diphenylsilylenebis(2-methylindenyl)titanium dichloride, tetramethyldisilylenebis(indenyl)titanium dichloride, tetramethyldisilylenebis(cyclopentadienyl)titanium dichloride, tetramethyldisilylene(3-methylcyclopentadienyl)(indenyl)titanium dichloride, dimethylsilylene(cyclopentadienyl)(3,4-dimethylcyclopentadienyl)titanium dichloride, dimethylsilylene(cyclopentadienyl)(trimethylcyclopentadienyl)titanium dichloride, dimethylsilylene(cyclopentadienyl)(tetramethylcyclopentadienyl)titanium dichloride, dimethylsilylene(cyclopentadienyl)(3,4-diethylcyclopentadienyl)titanium dichloride, dimethylsilylene(cyclopentadienyl)(trimethylcyclopentadienyl)titanium dichloride, dimethylsilylene(cyclopentadienyl)(tetraethylcyclopentadienyl)titanium dichloride, dimethylsilylene(cyclopentadienyl)(fluorenyl)titanium dichloride, dimethylsilylene(cyclopentadienyl)(2,7-di-t-butylfluorenyl)titanium dichloride, dimethylsilylene(cyclopentadienyl)(octahydrofluorenyl)titanium dichloride, dimethylsilylene(2-methylcyclopentadienyl)(fluorenyl)titanium dichloride, dimethylsilylene(2,5-dimethylcyclopentadienyl)(fluorenyl)titanium dichloride, dimethylsilylene(2-ethylcyclopentadienyl)(fluorenyl)titanium dichloride, dimethylsilylene(2,5-diethylcyclopentadienyl)(fluorenyl)titanium dichloride, diethylsilylene(2-methylcyclopentadienyl)(2',7'-di-t-butylfluorenyl)titanium dichloride, dimethylsilylene(2,5-dimethylcyclopentadienyl)(2',7'-di-t-butylfluorenyl)titanium dichloride, dimethylsilylene(2-ethylcyclopentadienyl)(2',7'-di-t-butylfluorenyl)titanium dichloride, dimethylsilylene(diethylcyclopentadienyl)(2,7-di-t-butylfluorenyl)titanium dichloride, dimethylsilylene(methylcyclopentadienyl)(octa hydrofluorenyl)titanium dichloride, dimethylsilylene(dimethylcyclopentadienyl)(octa hydrofluorenyl)titanium dichloride, dimethylsilylene(ethylcyclopentadienyl)(octa hydrofluorenyl)titanium dichloride, dimethylsilylene(diethylcyclopentadienyl)(octa hydrofluorenyl)titanium dichloride, dimethylsilylenebis(indenyl)zirconium dichloride, dimethylsilylenebis(4,5,6,7-tetrahydroindenyl)zirconium dichloride, dimethylsilylenebis(2-methylindenyl)zirconium dichloride, dimethylsilylenebis(2,4-dimethylindenyl)zirconium dichloride, dimethylsilylenebis(2,4-dimethylcyclopentadienyl)(3',5'-dimethylcyclopentadienyl)zirconium dichloride, dimethylsilylenebis(2-methyl-4,5-benzoindenyl)zirconium dichloride, dimethylsilylenebis(2-methyl-4-naphtylindenyl)zirconium dichloride, dimethylsilylenebis(2-methyl-4-phenylindenyl)zirconium dichloride, phenylmethylsilylenebis(indenyl)zirconium dichloride, phenylmethylsilylenebis(4,5,6,7-tetrahydroindenyl)zirconium dichloride, phenylmethylsilylenebis(2,4-dimethylindenyl)zirconium dichloride, phenylmethylsilylene(2,4-dimethylcyclopentadienyl)(3',5'-dimethylcyclopentadienyl)zirconium dichloride, phenylmethylsilylene(2,3,5-trimethylcyclopentadienyl)(21,41,51-trimethylcyclopentadienyl)zirconium dichloride, phenylmethylsilylenebis(tetramethylcyclopentadienyl)zirconium dichloride, diphenylsilylenebis(2,4-dimethylindenyl)zirconium dichloride, diphenylsilylenebis(indenyl)zirconium dichloride, diphenylsilylenebis(2-methylindenyl)zirconium dichloride, tetramethyldisilylenebis(indenyl)zirconium dichloride, tetramethyldisilylenebis(cyclopentadienyl)zirconium dichloride, tetramethyldisilylene(3-methylcyclopentadienyl)(indenyl)zirconium dichloride, dimethylsilylene(cyclopentadienyl)(3,4-dimethylcyclopentadienyl)zirconium dichloride, dimethylsilylene(cyclopentadienyl)(trimethylcyclopentadienyl)zirconium dichloride, dimethylsilylene(cyclopentadienyl)(tetramethylcyclopentadienyl)zirconium dichloride, dimethylsilylene(cyclopentadienyl)(3,4-diethylcyclopentadienyl)zirconium dichloride, dimethylsilylene(cyclopentadienyl)(triethylcyclopentadienyl)zirconium dichloride, dimethylsilylene(cyclopentadienyl)(tetraethylcyclopentadienyl)zirconium dichloride, dimethylsilylene(cyclopentadienyl)(fluorenyl)zirconium dichloride, dimethylsilylene(cyclopentadienyl)(2,7-di-t-butylfluorenyl)zirconium dichloride, dimethylsilylene(cyclopentadienyl)(octa hydrofluorenyl)zirconium dichloride, dimethylsilylene(2-methylcyclopentadienyl)(fluorenyl)zirconium dichloride, dimethylsilylene(2,5-dimethylcyclopentadienyl)(fluorenyl)zirconium dichloride, dimethylsilylene(2-ethylcyclopentadienyl)(fluorenyl)zirconium dichloride, dimethylsilylene(2,5-diethylcyclopentadienyl)(fluorenyl)zirconium dichloride, diethylsilylene(2-methylcyclopentadienyl)(2,7-di-t-butylfluorenyl)zirconium dichloride, dimethylsilylene(2,5-dimethylcyclopentadienyl)(2',7'-di-t-butylfluorenyl)zirconium dichloride, dimethylsilylene(2-ethylcyclopentadienyl)(2',7'-di-t-butylfluorenyl)zirconium dichloride, dimethylsilylene(diethylcyclopentadienyl)(2,7-di-t-butylfluorenyl)zirconium dichloride, dimethylsilylene (methylcyclopentadienyl)(octa hydrofluorenyl)zirconium dichloride, dimethylsilylene(dimethylcyclopentadienyl)(octa hydrofluorenyl)zirconium dichloride, dimethylsilylene (ethylcyclopentadienyl)(octa hydrofluorenyl)zirconium dichloride, dimethylsilylene(diethylcyclopentadienyl)(octa hydrofluorenyl)zirconium dichloride, dimethylsilylenebis(indenyl)hafnium dichloride, dimethylsilylenebis(4,5,6,7-tetrahydroindenyl)hafnium dichloride, dimethylsilylenebis(2-methylindenyl)hafnium dichloride, dimethylsilylenebis(2,4-dimethylindenyl)hafnium dichloride, dimethylsilylenebis(2,4-dimethylcyclopentadienyl)(3',5'-dimethylcyclopentadienyl)hafnium dichloride, dimethylsilylenebis(2-methyl-4,5-benzoindenyl)hafnium dichloride, dimethylsilylenebis(2-methyl-4-naphtylindenyl)hafnium dichloride, dimethylsilylenebis(2-methyl-4-phenylindenyl)hafnium dichloride, phenylmethylsilylenebis(indenyl)hafnium dichloride, phenylmethylsilylenebis(4,5,6,7-tetrahydroindenyl)hafnium dichloride, phenylmethylsilylenebis(2,4-dimethylindenyl)hafnium dichloride, phenylmethylsilylene(2,4-dimethylcyclopentadienyl)(3',5'-dimethylcyclopentadienyl)hafnium dichloride, phenylmethylsilylene(2,3,5-trimethylcyclopentadienyl)(2',4',5'-trimethylcyclopentadienyl)hafnium dichloride, phenylmethylsilylenebis(tetramethylcyclopentadienyl)hafnium dichloride, diphenylsilylenebis(2,4-dimethylindenyl)hafnium dichloride, diphenylsilylenebis(indenyl)hafnium dichloride, diphenylsilylenebis(2-methylindenyl)hafnium dichloride, tetramethyldisilylenebis(indenyl)hafnium dichloride, tetramethyldisilylenebis(cyclopentadienyl)hafnium dichloride, tetramethyldisilylene(3-methylcyclopentadienyl)(indenyl)hafnium dichloride, dimethylsilylene(cyclopentadienyl)(3,4-dimethylcyclopentadienyl)hafnium dichloride, dimethylsilylene(cyclopentadienyl)(trimethylcyclopentadienyl)hafnium dichloride, dimethylsilylene(cyclopentadienyl)(tetramethylcyclopentadienyl)hafnium dichloride, dimethylsilylene(cyclopentadienyl)(3,4-diethylcyclopentadienyl)hafnium dichloride, dimethylsilylene(cyclopentadienyl)(triethylcyclopentadienyl)hafnium dichloride, dimethylsilylene(cyclopentadienyl)(tetraethylcyclopentadienyl)hafnium dichloride, dimethylsilylene(cyclopentadienyl)(fluorenyl)hafnium dichloride, dimethylsilylene(cyclopentadienyl)(2,7-di-t-butylfluorenyl)hafnium dichloride, dimethylsilylene(cyclopentadienyl)(octa hydrofluorenyl)hafnium dichloride, dimethylsilylene(2-methylcyclopentadienyl)(fluorenyl)hafnium dichloride, dimethylsilylene(2,5-dimethylcyclopentadienyl)(fluorenyl)hafnium dichloride, dimethylsilylene(2-ethylcyclopentadienyl)(fluorenyl)hafnium dichloride, dimethylsilylene (2,5-diethylcyclopentadienyl)(fluorenyl)hafnium dichloride, diethylsilylene (2-methylcyclopentadienyl)(2',7'-di-t-butylfluorenyl)hafnium dichloride, dimethylsilylene (2,5-dimethylcyclopentadienyl)(2',7'-di-t-butylfluorenyl)hafnium dichloride, dimethylsilylene(2-ethylcyclopentadienyl)(2,7-di-t-butylfluorenyl)hafnium dichloride, dimethylsilylene(diethylcyclopentadienyl)(2,7-di-t-butylfluorenyl)hafnium dichloride, dimethylsilylene(methylcyclopentadienyl)(octahydrofluorenyl)hafnium dichloride, dimethylsilylene(dimethylcyclopentadienyl)(octa hydrofluorenyl)hafnium dichloride, dimethylsilylene(ethylcyclopentadienyl)(octa hydrofluorenyl)hafnium dichloride, and dimethylsilylene(diethylcyclopentadienyl)(octa hydrofluorenyl)hafnium dichloride.

(d) Transition-metal compounds having two conjugated five-membered cyclic ligands in which the two ligands are cross linked with a hydrocarbon group containing germanium, aluminium, boron, phosphorus, or nitrogen, such as dimethylgermylenebis(indenyl)titanium dichloride, dimethylgermylene(cyclopentadienyl)(fluorenyl)titanium dichloride, methylalumylenebis(indenyl)titanium dichloride, phenylalumylenebis(indenyl)titanium dichloride, phenylphosphylenebis(indenyl)titanium dichloride, ethylborenebis(indenyl)titanium dichloride, phenylalumylenebis(indenyl)titanium dichloride, phenylalumylene(cyclopentadienyl)(fluorenyl)titanium dichloride, dimethylgermylenebis(indenyl)zirconium dichloride, dimethylgermylene(cyclopentadienyl)(fluorenyl)zirconium dichloride, methylalumylenebis(indenyl)zirconium dichloride, phenylalumylenebis(indenyl)zirconium dichloride, phenylphosphylenebis(indenyl)zirconium dichloride, ethylborenebis(indenyl)zirconium dichloride, phenylamylenebis(indenyl)zirconium dichloride, phenylamylene(cyclopentadienyl)(fluorenyl)zirconium dichloride, dimethylgermylenebis(indenyl)hafnium dichloride, dimethylgermylene(cyclopentadienyl)(fluorenyl)hafnium dichloride, methylalumylenebis(indenyl)hafnium dichloride, phenylalumylenebis(indenyl)hafnium dichloride, phenylphosphylenebis(indenyl)hafnium dichloride, ethylborenebis(indenyl)hafnium dichloride, phenylamylenebis(indenyl)hafnium dichloride, and phenylamylene(cyclopentadienyl)(fluorenyl)hafnium dichloride.

(e) Transition-metal compounds having one conjugated five-membered cyclic ligand, such as pentamethylcyclopentadienyl(diphenylamino)titanium dichloride, indenyl(diphenylamino)titanium dichloride, pentamethylcyclopentadienyl-bis(trimethylsilyl)aminotitanium dichloride, pentamethylcyclopentadienylphenoxytitanium dichloride, dimethylsilylene(tetramethylcyclopentadienyl)-t-butylaminotitanium dichloride, dimethylsilylene(tetramethylcyclopentadienyl)phenylaminotitanium dichloride, dimethylsilylene(tetrahydroindenyl)decylaminotitanium dichloride, dimethylsilylene(tetrahydroindenyl)[bis(trimethylsilyl)amino]titanium dichloride, dimethylgermylene(tetramethylcyclopentadienyl)phenylaminotitanium dichloride, pentamethylcyclopentadienyltitanium trimethoxide, pentamethylcyclopentadienyltitanium trichloride, pentamethylcyclopentadienyl-bis(phenyl)aminozirconium dichloride, indenyl-bis(phenyl)aminozirconium dichloride, pentamethylcyclopentadienyl-bis(trimethylsilyl)aminozirconium dichloride, pentamethylcyclopentadienylphenoxyzirconium dichloride, dimethylsilylene(tetramethylcyclopentadienyl)-t-butylaminozirconium dichloride, dimethylsilylene(tetramethylcyclopentadienyl)phenylaminozirconium dichloride, dimethylsilylene(tetrahydroindenyl)decylaminozirconium dichloride, dimethylsilylene(tetrahydroindenyl)[bis(trimethylsilyl)amino]zirconium dichloride, dimethylgermylene(tetramethylcyclopentadienyl)phenylaminozirconium dichloride, pentamethylcyclopentadienylzirconium trimethoxide, pentamethylcyclopentadienylzirconium trichloride, pentamethylcyclopentadienyl-bis(phenyl)aminohafnium dichloride, indenyl-bis(phenyl)aminohafnium dichloride, pentamethylcyclopentadienyl-bis(trimethylsilyl)aminohafnium dichloride, pentamethylcyclopentadienylphenoxyhafnium dichloride, dimethylsilylene(tetramethylcyclopentadienyl)-t-butylaminohafnium dichloride, dimethylsilylene(tetramethylcyclopentadienyl)phenylaminohafnium dichloride, dimethylsilylene(tetrahydroindenyl)decylaminohafnium dichloride, dimethylsilylene(tetrahydroindenyl)[bis(trimethylsilyl)amino]hafnium dichloride, dimethylgermylene(tetramethylcyclopentadienyl)phenylaminohafnium dichloride, pentamethylcyclopentadienylhafnium trimethoxide, and pentamethylcyclopentadienylhafnium trichloride.

(f) Transition-metal compounds having two conjugated five-membered cyclic ligands in which the ligands are double-crosslinked, such as (1,1'-dimethylsilylene)(2,2'-isopropylidene)-bis(cyclopentadienyl)titanium dichloride, (1,1'-dimethylsilylene)(2,2'-dimethylsilylene)-bis(cyclopentadienyl)titanium dichloride, (1,1'-dimethylsilylene)(2,2'-isopropylidene)-bis(cyclopentadienyl)dimethyltitanium, (1,1'-dimethylsilylene)2,2'-isopropylidene)-bis(cyclopentadienyl)dibenzyltitanium, (1,1'-dimethylsilylene)(2,2'-isopropylidene)-bis(cyclopentadienyl)bis(trimethylsilyl)titanium, (1,1'-dimethylsilylene)(2,2'-isopropylidene)-bis(cyclopentadienyl)bis(trimethylsilylmethyl)titanium, (1,2'-dimethylsilylene)(2,1'-ethylene)-bis(indenyl)titanium dichloride, (1,1'-dimethylsilylene)(2,2'-ethylene)-bis(indenyl)titanium dichloride, (1,1'-ethylene)(2,2'-dimethylsilylene)-bis(indenyl)titanium dichloride, (1,1'-dimethylsilylene)(2,2'-cyclohexylidene)-bis(indenyl)titanium dichloride, (1,1'-dimethylsilylene)(2,2'-isopropylidene)-bis(cyclopentadienyl)zirconium dichloride, (1,1'-dimethylsilylene)(2,2'-dimethylsilylene)-bis(cyclopentadienyl)zirconium dichloride, (1,1'-dimethylsilylene)(2,2'-isopropylidene)-bis(cyclopentadienyl)dimethylzirconium, (1,1'-dimethylsilylene)(2,2'-isopropylidene)-bis(cyclopentadienyl)dibenzylzirconium, (1,1'-dimethylsilylene)(2,2'-isopropylidene)-bis(cyclopentadienyl)bis(trimethylsilyl)zirconium, (1,1'-dimethylsilylene)(2,2'-isopropylidene)-bis(cyclopentadienyl)bis(trimethylsilylmethyl)zirconium, (1,2'-dimethylsilylene)(2,1'-ethylene)-bis(indenyl)zirconium dichloride, (1,1'-dimethylsilylene)(2,2'-ethylene)-bis(indenyl)zirconium dichloride, (1,1'-ethylene)(2,2'-dimethylsilylene)-bis(indenyl)zirconium dichloride, (1,1'-dimethylsilylene) (2,2'-cyclohexylidene)-bis(indenyl)zirconium dichloride, (1,1'-dimethylsilylene) (2,2'-isopropylidene)-bis(cyclopentadienyl)hafnium dichloride, (1,1'-dimethylsilylene)(2,2'-dimethylsilylene)-bis(cyclopentadienyl)hafnium dichloride, (1,1'-dimethylsilylene) (2,2'-isopropylidene)-bis(cyclopentadienyl)dimethylhafnium, (1,1'-dimethylsilylene)(2,2'-isopropylidene)-bis(cyclopentadienyl)dibenzylhafnium, (1,1'-dimethylsilylene)(2,2'-isopropylidene)-bis(cyclopentadienyl)bis(trimethylsilyl)hafnium, (1,1'-dimethylsilylene) (2,2'-isopropylidene)-bis(cyclopentadienyl)bis(trimethylsilylmethyl)hafnium, (1,2'-dimethylsilylene) (2,1'-ethylene)-bis(indenyl)hafnium dichloride, (1,1'-dimethylsilylene) (2,2'-ethylene)-bis(indenyl)hafnium dichloride, (1,1'-ethylene) (2,2'-dimethylsilylene)-bis(indenyl)hafnium dichloride, and (1,1'-dimethylsilylene) (2,2'-cyclohexylidene)-bis(indenyl)hafnium dichloride.

(g) Further, the compounds described in the above (a) to (f) include compounds obtained by substituting chlorine atoms of the compounds described in the above (a) to (f) for any of a boron atom, an iodine atom, a hydrogen atom, a methyl group, a phenyl group, a benzyl group, a methoxy group, dimethyl amino group, or the like.

(h) Among the compounds described in the above (a) to (g), a particularly preferable compound is a transition metal compound having two conjugated five-membered ring ligands each cross linked with the silylene group of (c), where a transition metal is zirconium or titanium.

As a compound constructed of the (ii-1) cation out of the (ii) components constituting the catalyst and an anion in which multiple groups are bound to elements, any of compounds represented by the following formula (V) or (VI), but not particularly limited to, can be preferably used:

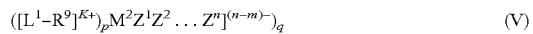  (V)

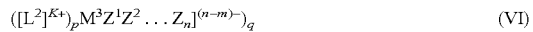  (VI)

where, $L^2$ is $M^4$, $R^{10}R^{11}M^5$, $R^{12}{}_3C$, $R^{13}R^{14}R^{15}R^{16}N$, or $R^{17}R^{18}R^{19}S$. $L^1$ is a Lewis base. Each of $M^2$ and $M^3$ is an element selected from Group 13, Group 14, Group 15, Group 16, and Group 17 of the periodic table. $M^4$ is an element selected from Group 1 to Group 11 of the periodic table. $M^5$ is an element selected from Group 8, Group 9, and Group 10 of the periodic table. Each of $Z^1$ to $Z^n$ represents a hydrogen atom, a dialkyl amino group, an alkoxy group having 1 to 20 carbon atoms, an aryloxy group having 6 to 20 carbon atoms, an alkyl group having 1 to 20 carbon atoms, an aryl, alkyl aryl, or aryl alkyl group having 6 to 20 carbon atoms, a halogen-substituted hydrocarbon group having 1 to 20 carbon atoms, an acyloxy group having 1 to 20 carbon atoms, an organic metalloid group, or a halogen atom. Two or more of $Z^1$ to $Z^n$ may be linked together to form a ring. $R^9$ represents a hydrogen atom, an alkyl group having 1 to 20 carbon atoms, or an aryl, alkyl aryl, or aryl alkyl group having 6 to 20 carbon atoms. Each of $R^{10}$ and $R^{11}$ represents a cyclopentadienyl group, a substituted cyclopentadienyl group, an indenyl group, or a fluorenyl group. $R^{12}$ represents, an aryl, alkyl aryl, or aryl alkyl group having 6 to 20 carbon atoms. Each of $R^{13}$ to $R^{19}$ represents a hydrogen atom, a halogen atom, an alkyl group having 1 to 20 carbon atoms, an aryl, alkyl aryl, or aryl alkyl group having 6 to 20 carbon atoms, a substituted alkyl group, or an organic metalloid group. m is an integer of 1 to 7 as an atomic valence of each of $M^2$ and $M^3$. n is an integer of 2 to 8. k is an integer of 1 to 7 as an ionic valence of each of $[L^1-R^9]$ and $[L^2]$, p is an integer of 1 or more, and q=(p×k)/(n−m)).

Specific examples of the above Lewis base ($L^1$) include: amines such as ammonia, methylamine, aniline, dimethylamine, diethylamine, N-methylaniline, diphenylamine, trimethylamine, triethylamine, tri-n-butylamine, N,N-dimethylaniline, methyl diphenyl amine, pyridine, p-bromo-N,N,dimethylaniline, and p-nitro-N,N-dimethylaniline; phosphines such as triethyl phosphine, triphenyl phosphine, and diphenyl phosphine; ethers such as dimethyl ether, diethyl ether, tetrahydrofuran, and dioxan; thioethers such as diethyl thioether and tetrahydrothiophene; and ester such as ethyl benzoate.

Specific examples of $M^2$ and $M^3$ include B and Al. Specific examples of $M^4$ include Na, Ag, and Cu. Specific examples of $M^5$ include Fe and Co. Specific examples of $Z^1$ to $Z^n$ include: dialkylamino groups such as a dimethylamino group and a diethyl amino group; alkoxy groups having 1 to 20 carbon atoms, such as a methoxy group, an ethoxy group, and an n-butoxy group; aryloxy groups having 6 to 20 carbon atoms, such as a phenoxy group, a 2,6-dimethyl phenoxy group, and a naphthyl oxy group; alkyl groups having 1 to 20 carbon atoms, such as a methyl group, an ethyl group, an n-propyl group, an isopropyl group, an n-butyl group, an n-octyl group, and a 2-ethyl hexyl group; an aryl group, an alkyl aryl group, or an aryl alkyl group, each having 6 to 20 carbon atoms, such as a phenyl group, a p-tolyl group, a benzyl group, a 4-tert-butyl phenyl group, a 2,6-dimethyl phenyl group, a 3,5-dimethyl phenyl group, a 2,4-dimethyl phenyl group, and a 2,3-dimethyl phenyl group; halogen-substituted hydrocarbon groups having 1 to 20 carbon atoms, such as a p-fluorophenyl group, a 3,5-difluorophenyl group, a pentachlorophenyl group, a 3,4,5-trifluoro phenyl group, a pentafluoro phenyl group, and a 3,5-di-(trifluoromethyl)phenyl group; halogen atoms such as F, Cl, Br, and I; organic metalloid groups such as 5-methyl antimony group, a trimethyl silyl group, a trimethyl germyl group, a diphenyl arsine group, a dicyclohexyl antimony group, and a diphenyl boron group.

Specific examples of the substituted cyclopentadienyl group of $R^{10}$ and $R^{11}$ include those substituted for alkyl groups such as a methyl cyclopentadienyl group, a butyl cyclopentadienyl group, and a pentamethyl cyclopentadienyl group. Herein, the alkyl group has generally 1 to 6 carbon atoms. The number of the substituted alkyl groups may be selected from integers of 1 to 5. Specific examples of $R^{12}$ include a methyl group, an ethyl group, and a phenyl group. Specific examples of $R^{13}$ to $R^{19}$ include a methyl group, an ethyl group, an n-propyl group, an n-butyl group, an isopropyl group, an n-octyl group, an isobutyl group, a phenyl group, a benzyl group, a p-tolyl group, a 4-t-butylphenyl group, a 2,6-dimethyl phenyl group, a cyclohexyl group, F, Cl, Br, and I.

Among the compounds represented by the above general formula (V) or (VI), preferable compounds are those in which $M^2$ and $M^3$ are boron, particularly those in which $M^2$ in the general formula (V) is boron. In the present invention, among the compounds represented by the above general formula (V) or (VI), specifically, the following compounds can be preferably used in particular.

Examples of the compound represented by the general formula (V) include triethylammonium tetraphenylborate, tri(n-butyl)ammonium tetraphenylborate, trimethylammonium tetraphenylborate, triethylammonium tetra(pentafluorophenyl)borate, tri(n-butyl)ammonium tetra(pentafluorophenyl)borate, anilinium tetra(pentafluorophenyl)borate, methylanilinium tetra(pentafluorophenyl)borate, dimethylanilinium tetra(pentafluorophenyl)borate, tetraphenylphosphonium tetra(pentafluorophenyl)borate, tetrabutylammonium tetra(pentafluorophenyl)borate, methyldiphenylammonium tetra(pentafluorophenyl)borate, triphenylammonium tetra(pentafluorophenyl)borate, pyridinium tetra(pentafluorophenyl)borate, dimethyl(m-nitroanilinium)tetra(pentafluorophenyl)borate, dimethyl(p-bromoanilinium)tetra(pentafluorophenyl)borate, (p-cyanopyridinium)tetra(pentafluorophenyl)borate, trimethylanilinium tetra(pentafluorophenyl)borate, (N-methylpyridinium)tetra(pentafluorophenyl)borate, trimethylsulfonium tetra(pentafluorophenyl)borate, (o-cyano-N-methylpyridinium)tetra(pentafluorophenyl)borate, dimethyldiphenylammonium tetra(pentafluorophenyl)borate, (p-cyano-N-benzylpyridinium)tetra(pentafluorophenyl)borate, methyltriphenylammonium tetra(pentafluorophenyl)borate, dimethylanilinium tetra(3,5-ditrifluoromethylphenyl)borate, and hexa fluoroarsenic acid triethylammonium.

Examples of the compound represented by the general formula (VI) include ferrocenium tetraphenylborate, silver tetraphenylborate, trityl tetraphenylborate, tetraethylammonium tetraphenylborate, methyltri(n-butyl)ammonium tetraphenylborate, benzyltri(n-butyl)ammonium tetraphenylborate, trimethylanilinium tetraphenylborate, dimethyldiphenylammonium tetraphenylborate, methyltriphenylammonium tetraphenylborate, methylpyridinium tetraphenylborate, benzylpyridinium tetraphenylborate, methyl(2-cyanopyridinium)tetraphenylborate, (tetraphenylporphyrin)manganese tetraphenylborate, trimethylsulfonium tetraphenylborate, benzyldimethylsulfonium tetraphenylborate, ferrocenium tetra(pentafluorophenyl)borate, decamethylferrocenium tetra(pentafluorophenyl)borate, acetylferrocenium tetra(pentafluorophenyl)borate, formylferrocenium tetra(pentafluorophenyl)borate, cyanoferrocenium tetra(pentafluorophenyl)borate, silver tetra(pentafluorophenyl)borate, trityl tetra(pentafluorophenyl)borate, lithium tetra(pentafluorophenyl)borate, (tetraethylammonium)tetrakis(pentafluorophenyl)borate, (methyltri(n-butyl)ammonium)tetrakis(pentafluorophenyl)borate, (benzyltri(n-butyl)ammonium)tetrakis(pentafluorophenyl)borate, trimethylanilinium tetrakis(pentafluorophenyl)borate, methyl(4-cyanopyridinium)tetrakis(pentafluorophenyl)borate, benzylpyridinium tetrakis(pentafluorophenyl)borate, benzylmethylsulfonium tetrakis(pentafluorophenyl)borate, tetrafluorosilver borate, hexa fluoroarsenical silver, and hexa fluorosilver antimonate. Compounds other than the compounds represented by the general formulae (V) and (VI), such as tri(pentafluorophenyl)boron, tri(3,5-di(trifluoromethyl)phenyl)boron, and triphenyl boron can also be used.

Among the components (ii) that constitute the catalyst, the organic aluminum compounds of (ii-2) include the compounds represented by the following general formula (VII), (VIII), or (IX):

$$R^{20}{}_r AlQ^3{}_{3-r} \quad (VII)$$

where $R^{20}$ represents a hydrocarbon group such as an alkyl group, an alkenyl group, an aryl group, or an aryl alkyl group, each having 1 to 20 carbon atoms, preferably 1 to 12 carbon atoms; $Q^3$ represents a hydrogen atom, an alkoxy group having 1 to 20 carbon atoms or a halogen atom; and r is a numeral of 1 to 3.

Specific examples of the organic aluminum compound represented by the above general formula (VII) include: trimethylaluminum, triethylaluminium, triisobutylaluminium, dimethylaluminum chloride, diethylaluminium chloride, methylaluminium dichloride, ethylaluminum dichloride, dimethylaluminum fluoride, diisobutylaluminum hydride, diethylaluminum hydride, and ethylaluminium sesquichloride.

A chain aluminoxan represented as follow:

[Chem 11]

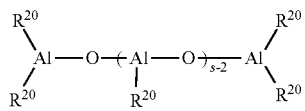
(VIII)

where $R^{20}$ is the same as one described above and s represents the degree of polymerization, typically in the range of 3 to 50.

A cyclic alkyl aluminoxan represented as follow:

[Chem 12]

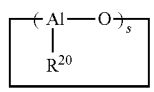
(IX)

where $R^{20}$ is the same as one described above and s represents the degree of polymerization, preferably in the range of 3 to 50.

A process for producing the above aluminoxane may be a process for making a contact between alkyl aluminum and a condensing agent such as water. However, the process is not particularly limited to such means, so the reaction may be proceeded according to the known process. For instance, the process may be a process in which an organic aluminum compound is dissolved in an organic solvent and then brought into contact with water, a process in which an organic aluminum compound is initially added at the time of polymerization and then added with water, a process in which an organic aluminum compound is reacted with crystal water contained in metal salt or the like or water to be adsorbed to an inorganic material or an organic material, or a process for allowing a reaction of tetraalkyl dialuminoxane with trialkyl aluminum and then reacting with water.

The catalyst used in the present invention may be one mainly containing the above component (i) and the above component (ii-1); one mainly containing the above component (i) and the above component (ii-2), and one mainly containing the above component (i), the above component (ii-1), and the above component (ii-2). When the (ii-1) component is used, the conditions of using the component (i) and the component (ii-1) are not limited. However, it is preferable that the ratio (mole ratio) of the component (i):the component (ii-1) be 1:0.01 to 1:100, particularly 1:1 to 1:10. In addition, the temperature used is preferably in the range of −100° C. to 250° C. and the pressure and the time can be arbitrarily defined. In addition, when the component (ii-2) is used, the used amount of the component (ii-2) is usually 1 to 1000 mol, preferably 3 to 600 mol with respect to 1 mol of the component (i). The use of the component (ii-2) can serve to improve the activity, but an excess amount thereof will lead to waste the organic aluminum compound. Note that, the component (i) and the component (ii-1) may be brought in to contact with each other in advance. The contacted product may be used after the separation and washing thereof, or may be contacted in a reaction system and then used. Further, the component (ii-2) may be brought into contact with the component (i), the component (ii-1), or a product of contacting the component (i) with the component (ii-1), and then used. The contact may be made in advance or in a reaction system.

The dimerization reaction of an α-olefin can be carried out in the presence of the α-olefin and the above catalyst and optionally in a hydrocarbon solvent at a temperature of 200° C. or less, preferably 10 to 100° C., while stirring for 4 to 200 hours, preferably 8 to 100 hours. The reaction pressure is usually ordinary pressure or compressed pressure. After completion of the reaction, it is deactivated with a compound having a hydroxyl group (e.g., methanol) and then optionally washed with acid (e.g., an aqueous solution of hydrochloric acid or sulfuric acid), followed by a vacuum distillation of the product (oil), thereby obtaining a dimer (vinylidene olefin) with high purity in high yield. The hydrocarbon solvent may be an aromatic hydrocarbon such as benzene, toluene, xylene, ethyl benzene, cumene, or cymene; an aliphatic hydrocarbon such as pentane, hexane, heptane, octane, decane, dode cane, hexadecane, or octadecane; an alicyclic hydrocarbon such as cyclopentane, cychohexane, cyclooctane, or methyl cyclopentane; and a halogenated hydrocarbon such as chloroform or dichloromethane. Any of these solvents may be used alone or may be used in combination with one or more other solvents.

An α-olefin dimer containing a vinylidene olefin (Compound 3) represented by the above general formula (3) in high concentration can be obtained by the dimerization reaction of an α-olefin in the presence of the metallocene complex catalyst.

Each of $R^{63}$ and $R^{64}$ in the general formula (3) is independently a hydrogen atom or a linear or branched alkyl group having 1 to 16 carbon atoms. In the present invention, preferably, each of $R^{63}$ and $R^{64}$ is one prepared using a linear α-olefin as a raw material of α-olefin and is independently a linear alkyl group having 8 to 16 carbon atoms.

(II) Step of Dimerizing Vinylidene Olefin (Compound 3)

In Patent Document 1, there is described a process for dimerizing a vinylidene olefin in small concentration, which is obtained by dimerizing a linear α-olefin using a Ziegler (organic aluminum compound) catalyst, in the presence of a Friedel craft catalyst (Lewis acid). In this method, according to the example, the Lewis acid such as aluminum chloride is dissolved in an aprotic polar solvent, which can dissolve the Lewis acid to carry out a reaction at an extremely low temperature (using a refrigerant); and after completion of the reaction, post-processing operations such as the collection of the solvent and the removal of the Lewis acid by acid cleaning are complicated.

In contrast, in the process of the present invention, 95% by mass or more of vinylidene olefin (Compound 3) obtained in the presence of a metallocene complex catalyst is used as a raw material. Besides, a solid acid catalyst is preferably used instead of the Lewis acid catalyst.

Examples of the solid acid catalyst employed in the dimerization step of the vinylidene olefin include: an acid zeolite, an acid zeolite molecular sieve, an acid-treated clay mineral, an acid-treated porous desiccant, or an ion-exchange resin. In other words, the solid acid catalyst may be an acid zeolite (e.g., HY); an acid zeolite molecular sieve having a pore size of about 5 to about 20 angstroms; one obtained by treating a clay mineral such as silica alumina, silica magnesia, montmorillonite, or halloysite with acid such as sulfuric acid; one obtained by placing hydrochloric acid, sulfuric acid, phosphoric acid, organic acids, $BF_3$, or the like on a porous desiccant such as a silica gel or an alumina gel; or a solid acid catalyst based on an ion exchange resin, such as a sulfonated product of a divinyl benzene styrene copolymer.

The added amount of the solid acid catalyst is 0.05 to 20 parts by mass with respect to 100 parts by mass of the feed amount of the vinylidene olefin. If the amount of the solid acid catalyst exceeds 20 parts by mass, it is uneconomical and a side reaction proceeds. The viscosity of a reaction liquid may increase and a decrease in yield may occur. If the amount is less than 0.05 parts by mass, the reaction efficiency decreases and a reaction time extends.

A preferable adding amount may be affected by the acidity of the solid acid catalyst. For example, in the case of the sulfur acid treatment of a montmorillonite-based clay mineral, the adding amount is 3 to 15 parts by mass with respect to 100 parts by mass of the feed of vinylidene olefin. For an ion-exchange resin based on a sulfonated product of divinylbenzene styrene copolymer, 1 to 5 parts by mass is preferable. Depending on the reaction conditions, two or more of these solid acid catalysts may be used in combination.

For example, in the case of an acid-treated clay mineral, such as montmorillonite or halloysite, the moisture content thereof may vary depending on the kind of the clay mineral, acid-treated conditions, storage conditions, and so on. The moisture content may be about 7 to 8% by mass in 100 g. The ion-exchange resin based on a sulfonated product of divinylbenzene styrene copolymer, which is used as a solid acid catalyst, may content a moisture of about 0.1 to 3% by mass. In the dimerization reaction of vinylidene olefin, the use of a solid acid catalyst having such a degree of the moisture content does not exert any significant bad influence. The process of solid-acid catalyst addition allows the dimerization reaction of a vinylidene olefin to proceed with successive addition of the solid acid catalyst to a reaction liquid. This case, however, is not preferable because of a decrease in production ratio of the compounds of the general formulae (4) or (5) in the same number of carbon atoms. The reaction temperature is usually 50° C. to 150° C. The reaction at 70° C. to 120° C. can lead to an increase in activity and selectivity, which is preferable. In addition, the reaction pressure is in the range of almost from the atmospheric pressure to 1 Mpa, but not affects on the reaction of pressure.

An α-olefin tetramer containing a compound (Compound 4) represented by the above general formula (4) or a compound (Compound 5) represented by the above general formula (5) in high concentration can be obtained by the dimerization reaction of the vinylidene olefin (Compound 3). Each of $R^{61}$ to $R^{64}$ in the general formula (4) or (5) is independently a hydrogen atom or a linear or branched alkyl group having 1 to 16 carbon atoms. In the present invention, a linear alkyl group having 8 to 16 carbon atoms is preferable (III) Step of Hydrogenating a Vinylidene Olefin Dimer In the step for hydrogenating a vinylidene-olefin dimer, the vinylidene-olefin dimer (Compound 4 or Compound 5) represented by the above general formula (4) or the above general formula (5) is subjected to gas-phase hydrogenation in the presence of a hydrogenation catalyst, thereby producing a saturated aliphatic hydrocarbon compound represented by the general formula (1). In this hydrogenation step, a gas-phase hydrogenation process commonly used in the art can be used. When a precious material such as palladium or platinum is used as a catalyst, the hydrogenation can be carried out at a reaction temperature of about 60 to 100° C. and a hydrogen pressure of about 0.1 to 1 MPa. If the catalyst is other than precious metals such as nickel, the conditions of both the reaction temperature and the hydrogen pressure should be tightened. In the case of a nickel-based catalyst, a reaction temperature of 150 to 250° C. and a hydrogen pressure of 1 to 20 MPa are preferable. In any case, the amount of the catalyst is generally in the range of 0.5 to parts by mass with respect to 1,000 parts by mass of the vinylidene olefin and the hydrogenation reaction will be then completed by 2 to 8-hour reaction. Further, the hydrogenation reaction of the vinylidene-olefin dimer quickly proceeds when the above hydrogenation catalyst is employed. However, even after a remarkable absorption of hydrogen is settled, a small amount of the remaining olefin is completely hydrogenated. Thus, any additional operation such as heat-up or pressure-up may be required.

As described above, the hydrogenated dimer of vinylidene olefin can be produced through the three reaction steps including: (I) dimerization of an α-olefin in the presence of a metallocene complex catalyst; (II) dimerization of a vinylidene olefin in the presence of a solid acid catalyst; and (III) gas-phase hydrogenation of a vinylidene-olefin dimer in the presence of a hydrogenation catalyst.

Note that, in the above reaction steps, the hydrogenated vinylidene olefin product, the hydrogenated trimer product, and the like can be obtained in addition to the hydrogenated vinylidene olefin dimer. Thus, the hydrogenated dimer may be isolated by distillation. The distillation may be a conventional simple distillation at a distillation temperature of about 190 to 260° C. and a pressure of about 25 to 75 kPa (0.2 to 0.6 Torr).

The principle product thus obtained is a saturated aliphatic hydrocarbon compound (Compound 1) having a structure represented by the following general formula (1):

[Chem 13]

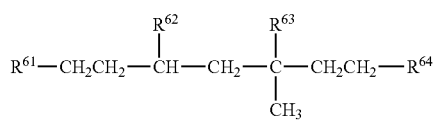
(1)

where $R^{61}$ to $R^{64}$ are identical with those described above.

In the present invention, a linear α-olefin is used as an α-olefin raw material. Each of the above $R^{61}$ to $R^{64}$ is independently a linear alkyl group having 8 to 16 carbon atoms. In other words, a saturated aliphatic hydrocarbon compound (Compound 1-a) having the structure represented by the general formula (1-a) is preferable:

[Chem 14]

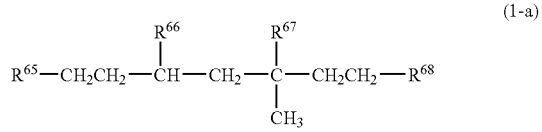
(1-a)

where $R^{65}$ to $R^{68}$ are identical with those described above.

In the above general formula (1-a), when each of $R^{65}$ to $R^{68}$ is a linear alkyl having 8 carbon atoms, the starting material (linear α-olefin) is 1-decene. Similarly, the starting materials are 1-dodecene for 10 carbon atoms, 1-tetradecene for 12 carbon atoms, 1-hexadecene for 14 carbon atoms, and 1-octadecene for 16 carbon atoms, and these hydrogenated vinylidene-olefin dimer can be used in a lubricant base oil and a heating medium. In the lubricant base oil demanded under the conditions in which low-temperature fluidity is essential, a hydrogenated vinylidene olefin dimer obtained using an α-olefin in which $R^{65}$ to $R^{68}$ are 8 and 10 to 12 carbon atoms, specifically 1-decene, 1-dodecene, or 1-tetradecene is suitable for a starting material.

Further, the present invention also provides a process for producing a saturated aliphatic hydrocarbon compound (Compound 2) represented by the general formula (2) in which an α-olefin is used as a raw material:

[Chem 15]

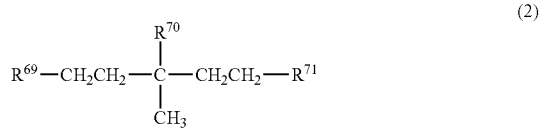
(2)

where $R^{69}$ represent a liner or branched alkyl group having 4 to 6 carbon atoms, $R^{70}$ and $R^{71}$ each represent independently a hydrogen atom or a liner or branched alkyl group having 1 to 16 carbon atoms, and the total number of carbon atoms in $R^{69}$ to $R^{71}$ is an integer of 3 to 48.

The process for producing this Compound 2 is characterized by including the steps of:

(IV) dimerizing an α-olefin in the presence of a metallocene complex catalyst to produce a vinylidene olefin;

(V) adding an α-olefin having 6 to 9 carbon atoms to the vinylidene olefin in the presence of an acid catalyst; and (VI) hydrogenating an α-olefin adduct obtained in the step (V).

(IV) Step of Producing Vinylidene Olefin

This step is the same as the step (I) of producing the vinylidene olefin as described in the process of producing the above Compound 1. An α-olefin is dimerized in a manner similar to the step (I), so a vinylidene olefin (Compound 3) can be selectively obtained in high yield.

(V) Step of Adding α-Olefin to Vinylidene Olefin (Compound 3)

In this step, an α-olefin having 6 to 9 carbon atoms is added to the vinylidene olefin (Compound 3) obtained in the above step (IV) in the presence of an acid catalyst.

The acid catalyst used in this addition reaction, the used amount of the acid catalyst, the reaction conditions thereof, and the like are equal to those in the step (II) of dimerizing the vinylidene olefin as described in the process of producing the above Compound 1. Examples of the α-olefin having 6 to 9 carbon atoms include 1-hexane, 1-hepten, 1-octen, and 1-nonen. These α-olefins may be linear or branched. Further, in the present invention, one kind of the α-olefins may be independently used or two or more of them may be used in combination.

This addition reaction can provide an unsaturated aliphatic hydrocarbon compound (Compound 6) represented by the general formula (6):

[Chem 16]

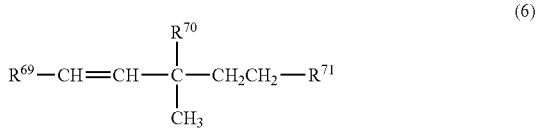

(6)

where $R^{69}$ to $R^{71}$ are identical with those described above.

(VI) Step of Hydrogenating Compound 6

This step is to hydrogenate Compound 6 obtained in the above step (V).

The catalyst used in the hydrogenation reaction and the reaction conditions thereof are equal to those in the step (III) of hydrogenation of vinylidene olefin dimer as described in the process of producing the above Compound 1.

The principle product thus obtained is a saturated aliphatic hydrocarbon compound (Compound 2) having a structure represented by the following general formula (2):

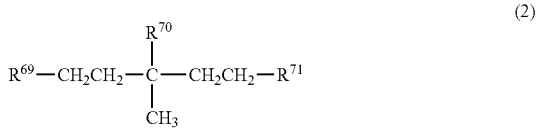

(2)

where $R^{69}$ to $R^{71}$ are identical with those described above.

The reaction liquid may be distilled if required to isolate the above Compound 2. This distillation may be a conventional simple distillation.

Next, the lubricant composition of the present invention will be described.

The lubricant composition of the present invention is characterized by including Compound 1 and/or Compound 2 obtained by the above method.

Among the above Compound 1 and Compound 2, Compound 1-a is preferable in terms of performance. In addition, each of $R^{65}$ to $R^{68}$ in Compound 1-a is preferably a linear alkyl group having 8 to 12 carbon atoms.

In particular, in the use of a lubricant, which is excellent in oxidation stability, thermal stability, and low-temperature fluidity, hydrogenated dimer products of vinylidene olefin from 1-decene and 1-dodecene are preferable. Further, the hydrogenated dimer product of vinylidene olefin from 1-decene is most preferable.

In other words, the principle product of the hydrogenated dimer product of vinylidene olefin induced from 1-decen in the presence of a metallocene complex catalyst is 11-methyl-11,13-dioctyl tricosane. Thus, one containing such a product at a concentration of 55% by mass or more in the saturated aliphatic hydrocarbon compound obtained from 1-decene may be preferably used as a lubricant base oil. If it is less than 55% by mass, the hydrogenated dimer product has poor distillation characteristics and an extended boiling point range. Thus, for example, if it is used in engine oil or compressor oil, a low-boiling composition vaporise and the lubricant base oil decreases in amount while increasing its viscosity, thereby accelerating the cycle of oil change. Further, when it is used in vacuum-pump oil, it acts as is the case with the above, and in addition it becomes difficult to secure the degree of vacuum.

Further, in the lubricant composition of the present invention, a saturated aliphatic hydrocarbon compound, which is obtained using 1-decene as a raw material, linear α-olefin and in which the content of 11-methyl-11,13-dioctyl tricosane is 65% by mass in the saturated aliphatic hydrocarbon compound having 40 carbon atoms, is used as a base oil, so a lubricant composition having a further improved performance can be obtained.

In the present invention, when the above Compound 1 and the above Compound 2 are used in a lubricant base oil to prepare a lubricant composition, various additives may be used together as far as the additives do not affect on the advantages of the present invention.

These additives include an antioxidant, an oiliness agent, an extreme pressure agent, a detergent-dispersant, a viscosity index improver, a rust preventing agent, a metal deactivator, and a defoaming agent. Each of these additives may be independently used or two or more of them may be used in combination.

The antioxidants include amine antioxidants, phenolic antioxidants, and sulfur antioxidants, which can be used in the conventional hydrocarbon synthetic lubricants. Each of these antioxidants may be independently used or two or more of them may be used in combination.

Examples of the amine-based antioxidant include monoalkyldiphenylamine-based compounds such as monooctyldiphenylamine and monononyldiphenylamine; dialkyldiphenylamine-based compounds such as 4,4'-dibutyldiphenylamine, 4,4'-dipentyldiphenylamine, 4,4'-dihexyldiphenylamine, 4,4'-diheptyldiphenylamine, 4,4'-dioctyldiphenylamine, and 4,4'-dinonyldiphenylamine; polyalkyldiphenylamine-based compounds such as tetrabutyldiphenylamine, tetrahexyldiphenylamine, tetraoctyldiphenylamine, and tetranonyldiphenylamine; and naphthylamine-based compounds such as α-naphthylamine, phenyl-α-naphthylamine, butylphenyl-α-naphthylamine, pentylphenyl-α-naphthylamine, hexylphenyl-α-naphthylamine, heptylphenyl-α-naphthylamine, octylphenyl-α-naphthylamine, and nonylphenyl-α-naphthylamine.

Examples of the phenol-based antioxidant include monophenol-based compounds such as 2,6-di-tert-butyl-4-methylphenol and 2,6-di-tert-butyl-4-ethylphenol; and diphenol-based compounds such as 4,4'-methylenebis(2,6-di-tert-butylphenol) and 2,2'-methylenebis(4-ethyl-6-tert-butylphenol). Examples of the sulfur-based antioxidant include thioterpene-based compounds such as 2,6-di-tert-butyl-4-(4,6-bis(octylthio)-1,3,5-triazin-2-ylamino)phenol, and a reactant of phosphorus penta sulfide and pinene; and dialkyl thiodipropionate such as dilauryl thiodipropionate and distearyl thiodipropionate.

The blending amounts of these antioxidants are usually about 0.01 to 10% by mass, preferably 0.03 to 5% by mass on the basis of the total amount of the lubricant.

The oiliness agents include fatty acid compounds such as aliphatic alcohols, fatty acids, and fatty acid metal salts; ester compounds such as polyol esters, sorbitan esters, and glycerides; and amine compounds such as aliphatic amines.

The aliphatic alcohols can be represented by the following general formula (I'):

(I')

where $R^{18}$ represents a group selected from an alkyl group, an alkenyl group, an alkyl aryl group, and an aryl alkyl group, each having 8 to 30 carbon atoms, preferably having 12 to 24 carbon atoms.

Examples of the alkyl group having 8 to 30 carbon atoms include various octyl groups, various nonyl groups, various decyl groups, various undecyl groups, various octadecyl groups, various dodecyl groups, and various hexadecyl groups. Examples of the alkenyl group having 8 to 30 carbon atoms include octadecenyl groups such as an octenyl group, a nonenyl group, a decenyl group, and an oleyl group. Examples of the alkylaryl group having 8 to 30 carbon atoms include various dimethylphenyl groups, various diethylphenyl groups, various dipropylphenyl groups, various methylnaphtyl groups, and various ethylnaphtyl groups. Examples of the arylalkyl group having 8 to 30 carbon atoms include a phenetyl group and a naphtyl methyl group. Of those, a stearyl group and an oleyl group as an n-octadecyl group are preferred.

The fatty acid compounds are compounds represented by the following general formula (II'):

$(R^{19}—COO)_nX^1$      (II')

where $R^{19}$ represents a group selected from an alkyl group, an alkenyl group, an alkyl aryl group, and an aryl alkyl group, each having 8 to 30 carbon atoms, preferably having 12 to 24 carbon atoms; and $X^1$ is a atom selected from H, K, Na, Mg, Ca, Al, Zn, Fe, Cu, and Ag.

The alkyl group, the alkenyl group, the alkyl aryl group, and the aryl alkyl group, each having 8 to 30 carbon atoms, for $R^{19}$ are the same as those described above. Among them, a stearyl group and an oleyl group are preferably used. $X^1$ is preferably H, K, Al, or Zn. n is an integer of 1 to 3.

The polyol esters include those obtained by ester reactions between polyvalent alcohols such as neopentylglycol, trimethylolpropane, and pentaerythritol, and fatty acids represented by the following general formula (III'):

$R^{20}—COOH$      (III')

where $R^{20}$ represents a group selected from an alkyl group, an alkenyl group, an alkyl aryl group, and an aryl alkyl group, each having 8 to 30 carbon atoms, preferably having 8 to 24 carbon atoms.

The alkyl group, the alkenyl group, the alkyl aryl group, and the aryl alkyl group, each having 8 to 30 carbon atoms, for $R^{20}$ are the same as those described above. Among them, an octyl group is particularly preferable.

The sorbitan esters are represented by the following general formula (IV'):

[Chem 18]

where $R^{21}$ to $R^{25}$ represents a group selected from H, OH, and $CH_2OCOR^{26}$; and $R^{26}$ represents an alkyl group or an alkenyl group having 9 to 30 carbon atoms, preferably 12 to 24 carbon atoms.

Examples of the alkyl group having 9 to 30 carbon atoms represented by $R^{26}$ include various nonyl groups, various decyl groups, various undecyl groups, various stearyl groups, various lauryl groups, and various palmitil groups. Examples of the alkenyl group having 9 to 30 carbon atoms include a nonenyl group, a decenyl group, and an octadecenyl group. Examples of a preferred aliphatic acid include lauric acid, stearic acid, palmitic acid, and oleic acid.

The glycerides include those represented by the following general formula (V'):

[Chem 19]

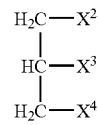

(V')

where $X^2$ to $X^4$ represent OH or $OCOR^{27}$; and $R^{27}$ represents an alkyl group or an alkenyl group having 8 to 30 carbon atoms, preferably 12 to 24 carbon atoms.

The alkyl group and the alkenyl group, each having 8 to 30 carbon atoms, for $R^{27}$ are the same as those described above. Preferable fatty acids include lauric acid, stearic acid, palmitic acid, and oleic acid.

The aliphatic amines include mono-substituted amines, di-substituted amines, and tri-substituted amines represented by the following general formula (VI'):

$R^{28}_mNH_{3-m}$      (VI')

where $R^{28}$ represents a group selected from an alkyl group and an alkenyl group, each having 3 to 30 carbon atoms, preferably 8 to 24 carbon atoms; an aryl group and an aryl alkyl group having 6 to 30 carbon atoms, preferably 6 to 15 carbon atoms; and a hydroxyalkyl group having 2 to 30 carbon atoms, preferably 2 to 18 carbon atoms; and m is an integer of 1 to 3.

Among the above $R^{28}$, each of the alkyl group and the alkenyl group may be linear, branched, or cyclic. The alkyl group and the alkenyl group, each having 3 to 30 carbon atoms, and the aryl group and the aryl alkyl group, each having 6 to 30 carbon atoms, of $R^{28}$ are the same as those described above. The hydroxyalkyl groups having 2 to 3 carbon atoms include a hydroxyethyl group and a hydroxypropyl group.

The mixing amounts of these oiliness agents are generally about 0.1 to 30% by mass, preferably 0.5 to 10% by mass on the basis of the total amount of the lubricant in terms of the advantage of the mixing.

The extreme pressure agents include a sulfur extreme pressure agent, a phosphorus extreme pressure agent, an extreme pressure agent containing sulfur and a metal, and an extreme pressure agent containing phosphorus and a metal. Each of these extreme pressure agents may be independently used or two or more of them may be used in combination. Any extreme pressure agent may be used as far as it contains a sulfur atom and/or a phosphorus atom in molecules and can exert load bearing characteristics and wear-resistance characteristics. The extreme pressure agents that contain sulfur atoms in molecules include sulfurized fat, sulfurized fatty acid, sulfurized ester, sulfurized olefin, dihydrocarvyl polysulphide, and a thiadiazole compound, an alkylthiocarbamoyl compound, a triazin compound, a thioterpenic compound, and a dialkyl thiodipropionate compound.

The sulfurized fats are those obtained by reacting sulfur or a sulfur-containing compound with fats (lard oil, whale oil, vegetable oil, fish oil, and the like) and the sulfur content thereof is, but not specifically limited to, generally suitable in the range of 5 to 30% by weight. Specific examples thereof include sulfurized lard, sulfurized oil of rapeseed, sulfurized castor oil, sulfurized soy oil, and sulfurized rice bran oil. An example of the sulfurized fatty acid may be an sulfurized oleic acid or an example of the sulfurized ester may be sulfurized methyl oleate or sulfurized rice bran fatty acid octyl.

The sulfurized olefins include compounds represented by the following general formula (VII'):

$$R^{29}-S_a-R^{30} \qquad (VII')$$

where $R^{29}$ represents an alkenyl group having 2 to 15 carbon atoms, preferably 4 to 8 carbon atoms; $R^{30}$ represents an alkyl group or an alkenyl group having 2 to 15 carbon atoms, preferably 4 to 8 carbon atoms; and a is an integer of 1 to 8, preferably 1 to 3.

This compound can be obtained by reacting an olefin having 2 to 15 carbon atoms or a dimer, a trimer or a tetramer thereof with a sulfurizing agent such as sulfur or sulfur chloride. The olefins having 2 to 15 carbon atoms preferably include propylene, isobutene, and diisobutene.

The dihydrocarvyl polysulfide is a compound represented by the following general formula (VIII'):

$$R^{31}-S_b-R^{32} \qquad (VIII')$$

where each of $R^{31}$ and $R^{32}$ represents an alkyl group or a cyclic alkyl group having 1 to 20 carbon atoms, preferably 4 to 18 carbon atoms, an aryl group having 6 to 20 carbon atoms, preferably 6 to 15 carbon atoms, an alkyl aryl group having 7 to 20 carbon atoms, preferably 7 to 15 carbon atoms, or an aryl alkyl group having 7 to 20 carbon atoms, preferably 7 to 15 carbon atoms, which may be identical with or different from each other; and b is an integer of 2 to 8, preferably 2 to 4.

Herein, if both $R^{31}$ and $R^{32}$ are alkyl groups, the compound is referred to as sulfurized alkyl.

Examples of $R^{31}$ and $R^{32}$ in the general formula (VIII') include a methyl group, an ethyl group, an n-propyl group, an isopropyl group, an n-butyl group, an isobutyl group, a sec-butyl group, a tert-butyl group, various pentyl groups, various hexyl groups, various heptyl groups, various octyl groups, various nonyl groups, various decyl groups, various dodecyl groups, a cyclohexyl group, a cyclooctyl group, a phenyl group, a naphtyl group, a tolyl group, a xylyl group, a benzyl group, and a phenethyl group.

Examples of the dihydrocarbyl polysulfide include preferably dibenzyl polysulfide, various dinonyl polysulfides, various didodecyl polysulfides, various dibutyl polysulfides, various dioctyl polysulfides, diphenyl polysulfide, and dicyclohexyl polysulfide.

Examples of the thiadiazole compound include 1,3,4-chiazole, 1,2,4-thiadiazole compound, and 1,4,5-chiadiazole compounds as represented by the following general formula (IX') or (X'):

[Chem 20]

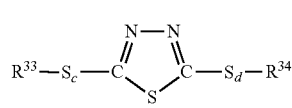

(IX')

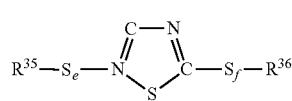

(X')

where each of $R^{33}$ to $R^{36}$ represents a hydrogen atom or a hydrocarbon group having 1 to 20 carbon atoms, preferably 4 to 13 carbon atoms; and each of c to f is an integer of 0 to 8, preferably 1 to 4.

Specific examples of the thiadiazole compound include preferably 2,5-bis(n-hexyldithio)-1,3,4-thiadiazole, 2,5-bis(n-octyldithio)-1,3,4-thiadiazole, 2,5-bis(n-nonyldithio)-1,3,4-thiadiazole, 2,5-bis(1,1,3,3-tetramethylbutyldithio)-1,3,4-thiadiazole, 3,5-bis(n-hexyldithio)-1,2,4-thiadiazole, 3,5-bis(n-octyldithio)-1,2,4-thiadiazole, 3,5-bis(n-nonyldithio)-1,2,4-thiadiazole, and 3,5-bis(1,1,3,3-tetramethylbutyldithio)-1,2,4-thiadiazole.

The alkyl thiocarbamoyl compounds, which can be preferably used, include those represented by the following general formula (XI'):

[Chem 21]

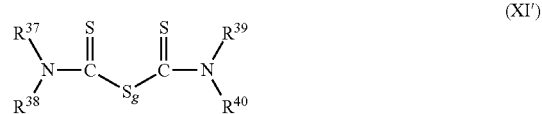

(XI')

where each of $R^{37}$ to $R^{40}$ represents an alkyl group having 1 to 20 carbon atoms, preferably 4 to 8 carbon atoms; and g is an integer of 1 to 8, preferably 1 to 3.

Specific examples of the alkyl thiocarbamoyl compound include bis(dimethyl thiocarbamoyl)monosulfide, bis(dibutyl thiocarbamoyl)monosulfide, bis(dimethyl thiocarbamoyl)disulfide, bis(dibutyl thiocarbamoyl)disulfide, bis(diamylthiocarbamoyl)disulfide, and bis(dioctylthiocarbamoyl)disulfide.

The extreme pressure agents, which contain sulfur, phosphorus, and a metal, include: zincdialkylthiocarbamate (Zn-DTC), molybdenum dialkylthiocarbamate (Mo-DTC), lead dialkylthiocarbamate, tin dialkylthiocarbamate, zinc dialkyldithiophosphate (Zn-DTP), molybdenum dialkyldithiophosphate (Mo-DTP), sodium sulfonate, and calcium sulfonate.

The typified extreme pressure agents, which include phosphorus in molecule, include phosphates esters and amine salts. The phosphates include phosphates, acidic phosphates, phosphites, and acidic phosphites, which are represented by the following general formulae (XII') to (XVI').

[Chem 22]

(XII')

(XIII')

(XIV')

(XV')

-continued

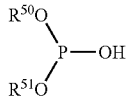
(XVI')

In the above general formulae (XII') to (XVI'), each of $R^{41}$ to $R^{51}$ represents a group selected from an alkyl group, an alkenyl group, an alkyl aryl group, and an aryl alkyl group, each having 4 to 30 carbon atoms, preferably 4 to 18 carbon atoms; and $R^{41}$ to $R^{51}$ may be identical with or different from one another.

Examples of a phosphate include triaryl phosphate, trialkyl phosphate, trialkylaryl phosphate, triarylalkyl phosphate, and trialkenyl phosphate. To be specific, triphenyl phosphate, tricresyl phosphate, benzyldiphenyl phosphate, ethyldiphenyl phosphate, tributyl phosphate, ethyldibutyl phosphate, cresyldiphenyl phosphate, dicresylphenyl phosphate, ethylphenyldiphenyl phosphate, diethylphenylphenyl phosphate, propylphenyldiphenyl phosphate, dipropylphenylphenyl phosphate, triethylphenyl phosphate, tripropylphenyl phosphate, butylphenyldiphenyl phosphate, dibutylphenylphenyl phosphate, tributylphenyl phosphate, trihexyl phosphate, tri(2-ethylhexyl)phosphate, tridecyl phosphate, trilauryl phosphate, trimyristyl phosphate, tripalmityl phosphate, tristearyl phosphate, and trioleyl phosphate.

Examples of an acid phosphate include 2-ethylhexylacid phosphate, ethylacid phosphate, butylacid phosphate, oleylacid phosphate, tetracosylacid phosphate, isodecylacid phosphate, laurylacid phosphate, tridecylacid phosphate, stearylacid phosphate, and isostearylacid phosphate.

Examples of a phosphite include triethyl phosphite, tributyl phosphite, triphenyl phosphite, tricresyl phosphite, tri(nonylphenyl)phosphite, tri(2-ethylhexyl)phosphite, tridecyl phosphite, trilauryl phosphite, triisooctyl phosphite, diphenylisodecyl phosphite, tristearyl phosphite, and trioleyl phosphite.

Examples of an acid phosphite include dibutylhydrogen phophite, dilaurylhydrogen phosphite, dioleylhydrogen phosphite, distearylhydrogen phosphite, and diphenylhydrogen phosphite. Further, examples of amines forming amine salts with those acid phosphites include, for example, a mono-substituted amine, a disubstituted amine, and a trisubstituted amine represented by the general formula (XVII'):

$$R^{52}{}_h NH_{3-h} \quad (XVII')$$

where $R^{52}$ represents an alkenyl group or an alkenyl group having 3 to 30 carbon atoms, preferably 4 to 18 carbon atoms, an aryl group or an aryl alkyl group having 6 to 30 carbon atoms, preferably 6 to 15 carbon atoms, or a hydroxy alkyl group having 2 to 30 carbon atoms, preferably 2 to 18 carbon atoms; h represents 1, 2 or 3; and when there are plurality of $R^{52}$, the plurality of $R^{52}$ may be identical with or different from one another.

The alkyl group or the alkenyl group having 3 to 30 carbon atoms in $R^{52}$ of the above general formula (XVII') may be linear, branched, or cyclic.

Examples of a monosubstituted amine include butylamine, pentylamine, hexylamine, cyclohexylamine, octylamine, laurylamine, stearylamine, oleylamine, and benzylamine. Examples of a disubstituted amine include dibutylamine, dipentylamine, dihexylamine, dicyclohexylamine, dioctylamine, dilaurylamine, distearylamine, dioleylamine, dibenzylamine, stearyl monoethanolamine, decyl monoethanolamine, hexyl monopropanolamine, benzyl monoethanolamine, phenyl monoethanolamine, and tolyl monopropanol. Examples of a trisubstituted amine include tributylamine, tripentylamine, trihexylamine, tricyclohexylamine, trioctylamine, trilaurylamine, tristearylamine, trioleylamine, tribenzylamine, dioleyl monoethanolamine, dilauryl monopropanolamine, dioctyl monoethanolamine, dihexyl monopropannolamine, dibutyl monopropanolamine, oleyl diethanolamine, stearyl dipropanolamine, lauryl diethanolamine, octyl dipropanolamine, butyl diethanolamine, benzyl diethanolamine, phenyl diethanolamine, tolyl dipropanolamine, xylyl diethanolamine, triethanolamine, and tripropanolamine.

The mixing amounts of these extreme pressure agents is generally about 0.01 to 30% by mass, more preferably 0.01 to 10% by mass on the basis of the total amount of the lubricant composition in terms of mixing advantage and economical advantages.

The detergent-dispersants include metal sulfonate, metal salicylate, metal phinate, and succinate imide. The mixing ratio of these detergent-dispersant is generally about 0.1 to 30% by mass, preferably 0.5 to 10% by weight on the basis of the total amount of the lubricant composition in terms of mixing advantage.

Examples of the viscosity index improver include polymethacrylate, dispersed polymethacrylate, olefinic copolymer (e.g., ethylene-propylene copolymer), dispersed olefinic copolymer, and styrene copolymer (e.g., styrene-diene hydrogenated copolymer). The mixing amounts of these viscosity index improvers are generally about 0.5 to 35% by mass, preferably 1 to 15% by mass on the basis of the total amount of the lubricant composition in terms of the advantage of mixing.

The rust preventing agents include metal sulfonates and succinate. The mixing amounts of these rust preventing agents are generally about 0.01 to 10% by mass, preferably 0.05 to 5% by mass on the basis of the total amount of the lubricant composition in terms of the advantage of mixing.

The metal deactivators include benzotriazole and thiadiazole. Preferable mixing amounts of these metal deactivators are generally about 0.01 to 10% by mass, preferably 0.01 to 1% by mass on the basis of the total amount of the lubricant composition in terms of the advantage of mixing.

The defoaming agents include methyl silicone oil, fluorosilicone oil, and polyacrylates. The mixing amounts of these defoaming agents are generally about 0.0005 to 0.01% by mass on the basis of the total amount of the lubricant composition in terms of the advantage of mixing.

The lubricant composition of the present invention can be used in combination with any of other base oils as far as the object of the present invention does not become compromised. The additional base oil may be suitably selected from mineral oil and synthetic oil.

The mineral oil may be, for example, distillate obtained by atmospheric distillation of paraffin-based crude oil, intermediate crude oil, or naphtenic crude oil or vacuum distillation of the residual oil from the atmospheric distillation; refined oil obtained by refining the distillate according to the conventional method. Specifically, the refined oil may be a solvent refined oil, a hydrogenated refined oil, a dewaxed oil, or a clay treated oil.

The synthetic oils include, for example, low-molecular weight polybutene, low-molecular weight polypropylene, α-olefin oligomer having 8 to 14 carbon atoms, and hydrides thereof; polyol esters (e.g., the fatty acid ester of trimethylolpropane and the fatty acid ester of pentaerythritol), dibasic acid ester, aromatic poly propylene carboxylate (e.g., trimellitate acid ester and pyromellitic acid ester); ester compounds such as phosphate; alkyl aroma-based compounds such as alkylbenzene and alkyl naphthalene; silicone oil; fluorine-based oil (e.g., fluorocarbon and perfluoropolyether).

Each of these and other base oils may be independently used or two or more of them may be used in combination.

The lubricant composition of the present invention is a nonpolar compound having an extremely small amount of evaporation and a high flash point, while having a low viscosity. Thus, the lubricant composition contains a base oil in which a saturated aliphatic hydrocarbon compound with a little influence on the resin or the elastomer is included as a principle component. Therefore, for example, it can be suitably used for a hydraulic pressure, a turbine, a machine tool, a bearing, a gear, a metal-working, and so on, and particularly for a bearing oil.

The present invention also provides the above bearing oil or a bearing using the oil. Examples of the bearing include a dynamic pressure fluid dynamic bearing, an oil impregnation bearing, and oil impregnation bearing provided with the dynamic pressure groove.

Spindle motors used in electrical apparatuses, particularly such as CD, DVD, HDD, and polygon scanner, has been speeded up year by year and at the present a high-speed rotation of 10,000 rpm or more is demanded.

Conventionally, roll bearings typified by ball bearings have been used in these spindle motors. However, non-contact fluid dynamic bearings and oil-impregnated sintered bearings of low cost are increasingly used in terms of performance and cost effectiveness. Performance (mainly running torque) at the time of high-speed rotations of these fluid dynamic bearings and oil-impregnated sintered bearings may be often determined based on the viscosity of a lubricant to be used. The running torque at the time of high-speed rotation tends to be lowered as the viscosity decreases.

When any of these lubricants is once enclosed in a bearing mechanism, they must maintain lubricity through the whole life in the state of no supply. Therefore, evaporative loss and destructive loss of lubricant must be avoided as much as possible.

The lubricant composition of the present invention has a characteristic of an extremely small amount of evaporation while having a low viscosity, so it can be very preferable to be used for lubricants of the fluid dynamic bearing and the oil-impregnated sintered bearing described above.

By the way, high-rotational accuracy and high reliability have been demanded on a HDD spindle motor used as a high-precision and high-definition recording device. As a result, the oil-impregnated sintered bearings have not been used because of having certain clearances to the rotational axis and causing rotation nonuniformity.

However, the oil-impregnated sintered bearing is remarkably excellent in workability and can be mass-produced. Therefore, as compared with a roll bearing or a fluid dynamic bearing, it can be supplied to the market with low cost. For this reason, the oil-impregnated sintered bearing has been also expected to be applied to the field of HDD apparatus where cost-effectiveness has been developed.

In order to solve such a disadvantage, for example, a dynamic-pressure type oil-impregnated sintered bearing unit has been developed. The dynamic-pressure type oil-impregnated sintered bearing unit is constructed of: a dynamic-pressure type oil-impregnated sintered bearing, in which a lateral pressure is applied to an oil-impregnated sintered bearing in a predetermined direction and a specific mechanism is provided for reducing the deflection of the rotation axis of a motor as much as possible while utilizing the characteristics of the oil-impregnated sintered bearing, formed with a sintered metal, a bearing body having a bearing surface opposite to the outer peripheral surface of the axis through a bearing gap and impregnated with a lubricant or a lubricating grease, in which the axis is non-contact supported by a dynamic-pressure action caused by a reciprocal rotation between the axis and the bearing body; a housing in which an opening is formed on the one side and the above dynamic oil-impregnated sintered bearing is provided to the inner surface of an inner diameter part; and a thrust bearing fixed on the other end of the housing and supporting the axis in the thrust direction, in which a dynamic pressure groove is formed on the surface of the thrust bearing by press-processing.

The present invention also provides gyral equipment having a bearing unit equipped with the above bearing.

An example of the gyral equipment may be a pressurized motor in which means for providing a motor axis with a lateral pressure in a predetermined direction, the motor axis being supported by an oil-containing bearing by powder-compacting sintering, displaces one of a pair of cores toward the motor axis, the core being fixed on a target position about the motor axis, and the oil-containing bearing is impregnated with the lubricant composition of the present invention.

Next, the above pressurized motor will be described with reference to the attached drawing. FIG. 1 is an enlarged cross-sectional view for illustrating an example of a spindle motor. Reference numeral 1 denotes a housing holder, 3 denotes a bearing, and 5 denotes a motor axis. The housing holder 1 is mounted on a base plate B or the like and provided with a cylindrical part 2. In addition, the outer peripheral surface of the cylindrical part 2 is wound with a coil 10 to form a laminated core 9 thereon. The bearing 3 is formed by powder-compacting molding of metal powder such as copper so as to have a size enough to be inserted into the housing holder 1 and then sintering the metal powder, followed by impregnation of the lubricant composition of the present invention. In addition, an inner clearance part 4 is formed in the middle of the axial hole so as to be constructed as a so-called inner-clearance/center-free type. Thus, a motor axis 5 can be supported by both ends in the longitudinal direction.

The motor axis 5 is constructed of a metal bar having an outer diameter that allows the motor axis 5 to be supported in the above bearing 3. A tip-side part located on the output side of the motor is integrally attached with a rotor 7 through a supporting member 6 so that it covers the outside of the coil 10 and the laminated core 9 and a magnet 8 are provided on the positions on the inner peripheral surface side corresponding to the above laminated core 9. Further, a hub is also integrally attached to the tip of the motor axis 5 to attach a rotation medium M of HDD.

Further, with respect to the motor axis 5 being supported by the oil-containing bearing 3 in which metal powders are complex-sintered, the one core 9 of the laminated cores 9 symmetrically fixed so as to sandwich the motor axis 5 is displaced from the line a position to the line b position at a distance of t-t toward the motor axis 5 (closed to a turn table 11). As the laminated core 6 is shifted, the rotor 7 being rotated at high speed can be always biased in the direction of the arrow P. As a result, the lateral pressure can be always imparted on the motor axis 5 in the predetermined direction (arrow-Y direction).

Therefore, the lateral pressure in the predetermined direction is imparted on the motor axis, so it can prevent the axial deflection against the oil-containing bearing prepared by the compression-sintering of metal powders.

EXAMPLES

The present invention will be described in detail with reference to examples of the present invention. The present invention will not be restricted to any of these examples.

Herein, for comparative examples, decene was dimerized using a Ziegler catalyst according to Patent Document 1. Subsequently, the dimers were then dimerized in the presence of a Friedel craft catalyst (Comparative Example 1) or in the presence of a commercially available decene oligomer with the $BF_3$ process (Comparative Example 2).

Performance evaluation of the lubricant base oils obtained by the respective examples and comparative examples and the lubricant compositions prepared by adding additive to the respective lubricant base oils were carried out as follows:

(1) Flash Point: Measured According to JIS K 2265

(2) Evaporation LOSS:

A sample (10 mg) was placed under nitrogen atmosphere (200 ml/min) and the sample was then heated up from 35° C. to 150° C. (200° C./min). Subsequently, the sample was kept at 150° C. for three hours and the mass reduction rate (%) of the sample was the measured.

(3) Viscosity Measurement

The kinematic viscosities of the sample at 40° C. and 100° C. were measured based on JIS K 2283, respectively. In addition, the measurement of viscosity index was performed based on JIS K 2283.

(4) Thermal Stability Test

A thermal stability test was performed at 170° C. for 48 hours based on JIS K 2540 and the presence or absence of sludge was confirmed by visual observation.

(5) RBOT Value (Oxidation Degradation Test)

A rotating bomb oxidation test (RBOT) for obtaining an index that represents the degree of oxidation degradation was performed based on JIS K 2514. Time (minute) to reach a terminal point of pressure drop was measured.

(6) Lubrication Performance (Wear Test)

Based on ASTM D 2783, a test was performed at a load of 392 N, a rotational frequency of 1,200 rpm, and an oil temperature of 80° C. for 60 minutes. The diameters of wear signs of three ½-inch balls were averaged to calculate the average wear diameter (mm).

(7) 5% by Mass Loss-in-Quantity Temperature by Thermal Analysis

A temperature at which a 5% by mass is lost from the initial mass was measured by heating up to 10° C./min using a thermal analyzer. The higher the 5% by mass loss-in-quantity temperature becomes, the excellent the evaporative resistance and the thermal resistance become.

(8) 5% by Mass Distillation Temperature by Vacuum Distillation

Based on JIS K 2254, distillation was carried out at a vacuum degree of 133 Pa and 5% by mass distillation temperature was then measured, followed by converting the measured temperature into the temperature under atmospheric pressure. The higher the temperature is, the smaller the evaporation loss occurs.

Example 1

(1) Dimerization of 1-decene with Metallocene Complex

In a three-necked flask (content volume of 5 L) purged with nitrogen, 3.0 kg of 1-decene, 0.9 g (3 mmol) of bis-(cyclopentadienyl)zirconium dichloride (also referred to as zirconocene dichloride) provided as a metallocene complex, and 8 ml (converted to Al) of methyl aluminoxane (manufactured by ALBEMARLE Corporation) were sequentially added in this order, followed by stirring at room temperature (20° C. or less). A reaction solution was changed from yellow to dark reddish-brown. After 48 hours from the start of the reaction, the reaction was terminated by the addition of methanol. Subsequently, an aqueous hydrochloric acid solution was added to the reaction solution to wash an organic layer. After that, the organic layer was subjected to vacuum distillation, thereby obtaining 2.5 kg of a distillated fraction (decene dimer) with a boiling point of 120 to 125° C./26.6 Pa (0.2 Torr). The distilled fraction was subjected to gas chromatographic analysis. As a result, the decene dimer has a concentration of 99% by mass and the percentage of vinylidene olefin in the decene dimer was 97 mol %.

(2) Dimerization and Hydrogenation of Vinylidene Olefin

In a 5-litter three-necked flask purged with nitrogen, 2.5 kg of the dimer obtained by the above item and 250 g of Monomorillonite K-10 (manufactured by Aldrich Corporation) were added and mixed at room temperature, followed by heating up to 110° C. while stirring. The reaction was carried out for 9 hours at that temperature. After that, the flask was cooled down and the montmorillonite (the catalyst) was filtrated at room temperature. Subsequently, the dimer reaction product was transferred to an autoclave (content volume of 5 L) and then added with 5 g of palladium alumina (5% by mass). The flask is purged with nitrogen and then purged with hydrogen, followed by heating up. A hydrogenation reaction was carried out at a hydrogen pressure of 0.8 MPa for 8 hours. After confirming that any hydrogen absorption does not occur any more, the flask was cooled down and the pressure thereof was relieved. The hydrogenated product was taken out of the autoclave. The catalyst was filtrated out of the hydrogenated product, thereby obtaining 2.2 kg of a clear and color less oily product. The oily product was subjected to gas chromatographic analysis and found out that saturated hydrocarbons of 20, 40, and 60 carbon atoms were generated at a ratio of 45% by mass, 52% by mass, and 3% by mass, respectively.

(3) Isolation and Identification of 11-methyl-11,13-dioctyl Tricosane

In a distillation flask (content volume of 5 L) immersed in a silicon oil bath, 2.2 kg of the oily product of the above item was transferred and the vacuum degree thereof was set to 26.6 Pa (0.2 torr). The oil bath was heated from room temperature to 150° C., followed by vacuum distillation. After distilling out the saturated hydrocarbon having 20 carbon atoms at 150° C., the flask was further heated and subjected to pressure reduction at 190° C. for 30 minutes at 26.6 Pa (0.2 torr). The distilled residue was 1.2 kg (40% crude yield of the whole step) and then analyzed by gas chromatography. The carbon hydrate with 20 carbon atoms was 0.3% by mass, the carbon hydrate with 40 carbon atoms was 92.7% by mass, the carbon hydrate with 60 carbon atoms was 7.0% by mass.

Subsequently, three fractions of the distilled residue of the distillation were obtained by preparative GPC and 11-methyl-11,13-dioctyl tricosane, a primary product with 40 carbon atoms, was isolated. The product was confirmed and the production ratio thereof was measured. The operation conditions of preparative GPC are as follows: Device: LC-918, Mobile phase: chloroform, 3.8 ml/min, and Column: two columns of JAIGEL-2H (Japan Analytical Industry, CO., Ltd.). After isolating the desired component, it was subjected to GC/MAS.

The operation conditions of the GC/MAS were as follows: Column: HP-5MS (0.25 mm×30 m, 0.25 μm of film thickness), Oven: 120° C. (2 min)-20° C./min-34° C. (5 min).

From a parent peak of m/z=562 and a main fragment of m/z=281, it was found that the compound was a dimer (hydrogenated product) of 2-octyl-1-dodecene (molecular weight of 280). Next, it was subjected to a long-range correlated analysis with $C^{13}$-NMR. The analysis profile was shown in FIG. 1. From this analysis, it was found that the tertiary carbon (e) and the quaternary carbon (b) are joined together on both sides of one methylene (d) and a methyl group (a) is connected with the quaternary carbon (b). Thus, the structure of the principle product was found to be 11-methyl-11,13-dioctyl tricosane ($R^{61}$ to $R^{64}$ are alkyl groups of 8 carbon atoms in Compound 1).

Further, the produced amount of the tricosane was quantitatively assayed by gas chromatography (under the same conditions as those employed in GC/MAS). As a result, the content (production rate) of 11-methyl-11,13-dioctyl tricosane in the product with 40-carbon atoms was 76% by mass. The percentage occupied in the distilled residue was 70% by mass. Therefore, the yield of the tricosane was calculated so that the total process yield from the raw-material decene was 28% by mass and the yield from the vinylidene olefin was 35% by mass.

(4) Comparison Between Decene Oligomer with Ziegler Catalyst and Commercial Decene Oligomer with $BF_3$ Process Results of the comparison with decene oligomer in the presence of Ziegler catalyst are shown in Table 1 and results of the comparison with commercial decene oligomer by $BF_3$ process are shown in Table 2.

Note that the comparison with decene oligomer in the presence of Zieger catalyst was carried out as a comparison for process, so the comparison was made with respect to the yield, flash point, and the evaporation loss of 11-methyl-11,13-dioctyl tricosane.

In the comparison with the commercial decene oligomer by the $BF_3$ process, the evaluation for base oil (oligomer, Example 1A) and the evaluation for lubricant composition (Example 1B) added with additives were carried out, respectively.

The additives and the adding among thereof used in the lubricant composition are as follows.
(Base oil: 98.44% by mass) Adding amount (% by mass)
(1) Antioxidant A: Di-t-butyl p-cresol 0.5
(2) Antioxidant B: Di-octyl di-phenylamine 0.5
(3) Extream pressure agent: Tricresyl phosphate 0.5
(4) Rust preventing agent: Alkenyl succiante 0.05
(5) Metal deactivatoar: Benzotriazole 0.005
(6) Defoaming agent: Dimethyl silicone oil 0.005

Comparative Example 1

Process in the Presence of Zieger Catalyst (1) Dimerization of Linear α-olefin (Dimerization of 1-decene in the Presence of Triethyl Aluminum)

In an autoclave (content volume of 1.0 L) purged with nitrogen, 1-decene (300 g) and triethyl aluminum (7.3 g, 64 mmol) were added under nitrogen gas flow and heated at 170° C. for 48 hours. After the reaction, the reaction solution was cooled to room temperature and then stirred under nitrogen atmosphere while gradually adding methanol to the reaction solution. Next, the content was taken out of the flask and then washed with an aqueous hydrochloric acid solution, thereby obtaining an organic layer. The vacuum distillation was performed, thereby obtaining 240 g of distilled fraction (decene dimer) with a boiling point of 120 to 125° C./2.66×10$^{-3}$ Pa (0.2 torr). The concentration of the dimer was 98% by mass and the ratio of vinylidene olefin in the dimer was 86% by mass.

(2) Dimerization and Hydrogenation of Vinylidene Olefin

In a 500-ml three-necked flask purged with nitrogen, 240 g of the dimer prepared by the above item and 24 g of Montmorillonite K-10 (manufactured by Aldrich Corporation) were added and blended at room temperature. After that, the reaction liquid was heated to 110° C. while stirring. The reaction was performed at that temperature for 9 hours. The following operations were carried out based on the item (2) of Example 1. As a result, 210 g of a clear and color less oily product was obtained. The oily product was subjected to gas chromatographic analysis. As a result, saturated hydrocarbons with 20 carbon atoms, 40 carbon atoms, and 60 carbon atoms are generated at a ratio of 51% by mass, 41% by mass, and 8% by mass, respectively.

(3) Production Rate and Yield of 11-methyl-11,13-dioctyl tricosane

A hydrogenated product was distilled according to the item (3) of Example 1, thereby obtaining 102 g of oily product (34% crude yield from the whole step) as a distilled fraction. The resulting fraction was subjected to gas chromatographic analysis. As a result, the hydrocarbon with 20 carbon atoms was 0.4% by mass, hydrocarbon with 40 carbon atoms was 83.1% by mass, and hydrocarbon with 60 carbons are 15.5% by mass.

Further, the amount of the generated tricosane was quantitatively assayed by gas chromatography. As a result, the content (production rate) of 11-methyl-11,13-dioctyl tricosane occupied in the product having 40 carbon atoms was 62% by mass, the ratio thereof occupied in the distilled residue (the product of 40 or more carbon atoms) was 52% by mass.

Therefore, the yield of the tricosane was calculated so that the total process yield from the raw-material decene was 18% by mass and the yield from the vinylidene olefin was 22% by mass.

A comparison result with a case where the metallocene catalyst was used is shown in Table 1.

Example 2

(1) Dimerization of 1-decene in the Presence of Metallocene Complex

In a 5-L three-necked flask purged with nitrogen, 1-decene (3.0 kg), bis-(pentamethyl cyclopentadimethyl)zirconium dichloride (0.17 g, 0.4 mmol), dimethyl anilinium salt of tetrakispentafluorophenyl borate (0.34 g, 0.4 mmol), and tri-isobutyl aluminum (manufactured by Toso Aquzo Co., Ltd., 40 mmol) were sequentially added at room temperature and then stirred at a reaction temperature of 80° C. After reacting for 8 hours, the reaction was terminated by the addition methanol. Subsequently, an aqueous hydrochloric acid solution was added to the reaction solution to wash an organic layer. Next, the organic layer was subjected to vacuum distillation, there by obtaining 1.2 kg of a distilled fraction (decene dimer) having a boiling point of 120 to 125° C./26.6 Pa (0.2 Torr). When the distilled fraction was subjected to a gas-chromatic analysis, the concentration of the dimer was 98% by mass and the ratio of divalent vinylidene olefin ratio in dimer was 95% by mass.

(2) Dimerization and Hydrogeneration of Vinylidene Olefin

Based on the item (2) of Example 1, 1.2 kg of the dimer and 120 g of Montmorillonite K-10 (manufactured by Aldrich Corporation) were mixed together and then heated to 110° C., followed by reacting for 9 hours at that temperature. Subsequently, the vinylidene dimer was transferred to an autoclave (content volume of 3 L) and hydrogenated with palladium alumina (5% by mass), thereby obtaining 1.1 kg of a clear and color less oily product. The oily product was subjected to gas chromatographic analysis. As a result, saturated hydrocarbons with 20 carbon atoms, 40 carbon atoms, and 60 carbon atoms were generated at a ratio of 46% by mass, 51% by mass, and 3% by mass, respectively.

(3) Production Rate and Yield of 11-methyl-11,13-dioctyl Tricosane

Based on the item (3) of Example 1, the hydrogenated product was distilled and a distilled residue having the composition of 0.4% by mass of hydrocarbon with 20 carbon atoms, 92.5% by mass of hydrocarbon with 40 carbon atoms, and 7.1% by mass of hydrocarbon with 60 carbon atoms was obtained. The distilled residue was analyzed and found that the content (production rate) of 11-methyl-11,13-dioctyl tricosane occupied in the hydrocarbon product with 40 carbon atoms was 75% by mass, while the ratio thereof occupied in the distilled residue of tricosane (the product with 40 or more carbon atoms) was 69%.

The result of comparison with the use of the Ziegler catalyst is shown in Table 1. In the case of the Ziegler catalyst, the content of vinylidene olefin, which is a dimer of the raw material decene in the step (I), is low. Thus, even after further dimerization and hydrogenation, the content of decene tetramer ($C_{40}$) becomes low. In addition, the $C_{40}$ base oil prepared using the metallocene complex catalyst of the present invention shows a higher flash point and lower evaporation loss, thereby resulting in more excellent base oil for compressor oil or vacuum pomp oil, compared with one prepared using the conventional Ziegler catalyst.

TABLE 1

| | Example 1 | Comparative Example 1 | Example 2 |
|---|---|---|---|
| (Production process: catalyst) | Metallocene | Ziegler | Metallocene |
| Product in Step (I) (% by mass) | | | |
| Decene dimer concentration | 99 | 98 | 98 |
| Ratio of vinylidene olefin in decene dimer | 97 | 86 | 95 |
| Product in step (III) (% by mass) | | | |
| $C_{20}$ | 45 | 51 | 46 |
| $C_{40}$ | 52 | 41 | 51 |
| $C_{60}$ | 3 | 8 | 3 |
| (Lubricant base oil composition: % by mass) | | | |
| $C_{20}$ | 0.3 | 0.4 | 0.4 |
| $C_{40}$ | 92.7 | 83.1 | 92.5 |
| $C_{60}$ | 7.0 | 15.5 | 7.1 |
| 11-methyl-11,13-dioctyltricosane/($C_{40}$ + $C_{60}$ + $C_{80}$) | 70 | 52 | 69 |
| 11-methyl-11,13-dioctyltricosane/$C_{40}$ | 76 | 62 | 75 |
| (Performance evaluation) | | | |
| (1) Flash point (° C.) | 266 | 261 | 266 |
| (2) Evaporation loss (% by mass) | 0.2 | 0.4 | 0.2 |

Comparative Example 2

Commercial Decene Oligomer Prepared by $BF_3$ Process

A poly-alpha-olefin manufactured by Amoco Co., Ltd. was used as a commercial decene oligomer prepared by the $BF_3$ process and then employed in comparison as a base oil (oligomer) and a lubricant composition. In the lubricant composition, a used additive and an added amount thereof are identical with those described in the item (4) of Example 1.

The results of the comparison with Example 1 are represented in Table 2. Example 1A and Comparative Example 2A are evaluated with respect to the base oil (oligomer). Example 1B and Comparative Example 2B are evaluated with respect to the lubricant composition to which an additive was added.

As is evident from the evaluation results shown in Table 2, even though having low viscosity, the flash point of the lubricant base oil ($C_{40}$) of Example 1A is higher than that of poly α-olefin prepared by the conventional $BF_3$ catalyst (Comparative Example 2A). Also, 5% by mass loss-in-quantity temperature is high when measured by the differential thermal analysis and has low evaporativity and excellent thermal resistance. Further, the lubricant composition of Example 1B shows no sludge in the thermal stability test while having the characteristics as described above. Besides, it shows a small diameter of wear sign in the wear test. Therefore, it is found that the performance of the lubricant composition of Example 1B can be favorably compared with that of the lubricant composition (Comparative Example 2B) using the poly α-olefin prepared by the conventional $BF_3$ process.

On the other hand, as shown in Comparative Example 2A and Comparative Example 2B, the conventional poly α-olefin prepared by the conventional $BF_3$ process shows a low flash point and a low 5% by mass loss-in-quantity temperature in the differential thermal analysis. Therefore, the conventional one can be considered insufficient in low evaporativity, compared with those of Example 1A and Example 1B, and found to be inappropriate to be employed as vacuum pump oil, where the light fraction thereof should be prevented from volatilizing, and compressor oil, which can be used at high temperature.

Comparative Example 3

An Other Process in the Presence of Metallocene Catalyst: Tetramer Formation of 1-decene In the item (1) of Example 1, bis(n-octadecyl cyclopentadienyl)zirconium dichloride was used instead of zirconocene chloride. After that, the formation of 1-decene tetramer was carried out in a manner similar to the item (1) of Example 1 and a hydrogenation reaction was then carried out in a manner similar to the hydrogenation in the item (2) of Example 1, thereby obtaining 0.25 kg of the hydrogenated product of a decene oligomer with a boiling point of 190 to 240° C./26.6 Pa (0.2 Torr).

Subsequently, the resulting fraction was subjected to gas chromatographic analysis, resulting in a product different from the compound isolated in the item (3) of Example 1. However, the presence of $C_{40}$ component in the product was found by NMR analysis. In other words, when the production of 1-decene tetramer was directly performed in the presence of the metallocene catalyst, the yield of the $C_{40}$ was extremely decreased as low as 8% by mass. As a result, large amounts of light fractions ($C_{20}$ and $C_{30}$) were generated.

Examples 3 to 8 and Comparative Example 4

Lubricants or lubricant compositions formulated as shown in Table 3 were prepared and their properties and performances were evaluated. The results are shown in Table 3. Further, the data of Example 1B and Comparative Example 2B was also described in Table 3.

TABLE 2

Table 2

| | Example 1A | Comparative Example 2A | Example 1B | Comparative Example 2B |
|---|---|---|---|---|
| (Production process) | Metallocene process | $BF_3$ process | Metallocene process | $BF_3$ process |
| | (Lubricant base oil) | | (Lubricant composition) | |
| (Performance evaluation) | | | | |
| (1) Flash point (° C.) | 266 | 236 | 262 | 233 |
| (2) Kinematic viscosity (mm²/s) | 40.92 | 46.74 | 42.15 | 47.97 |
| 40° C. | | | | |
| 100° C. | 7.1 | 7.84 | 7.15 | 7.84 |
| (3) Viscosity index | 135 | 137 | 132 | 132 |
| (4) Thermal stability (presence or absence of sludge) | Absence | Absence | Absence | Absence |
| (5) RBOT value (oxidation degradation test: min) | 48 | 32 | 1024 | 1012 |
| (6) Lubricating performance (average wear sign: mm) | 0.62 | 0.64 | 0.37 | 0.39 |
| (7) 5% by mass loss-in-quantity temperature (° C.) in thermal analysis | 287 | 265 | 284 | 261 |
| (8) 5% by mass distillation temperature (° C.) in vacuum distillation | 490 | 426 | 487 | 422 |

TABLE 3

Table 3-1

|  |  |  | Example |  |  |  |  |
|---|---|---|---|---|---|---|---|
|  |  |  | 1B | 3 | 4 | 5 | 6 |
| Applied oil species |  |  | Hydraulic fluid | Turbine oil | Bearing oil | Gear oil | Machine oil |
| Component composition (% by mass) | Base oil | Acid catalyst PAO [1)] | — | — | — | — | — |
|  |  | Metallocene PAO [2)] | 98.44 | 99.44 | 98.44 | 97.44 | 98.14 |
|  | Additives | Phenol-based antioxidant [3)] | 0.5 | 0.2 | 0.2 | 0.2 | 0.3 |
|  |  | Amine-based antioxidant 1 [4)] | 0.5 | 0.3 | 0.3 | 0.3 | — |
|  |  | Amine-based antioxidant 2 [5)] | — | — | — | — | — |
|  |  | Phosphate 1 [6)] | 0.5 | — | — | — | — |
|  |  | Phosphate 2 [7)] | — | — | — | — | 0.5 |
|  |  | Phosphate amine [8)] | — | — | — | 1.0 | — |
|  |  | Sulfur-based extreme-pressure agent [9)] | — | — | — | 1.0 | — |
|  |  | Sulfur-based extreme-pressure agent [10)] | — | — | — | — | 1.0 |
|  |  | Metal-based extreme-pressure agent [11)] | — | — | 1.0 | — | — |
|  |  | Rust preventing agent [12)] | 0.05 | 0.05 | 0.05 | 0.05 | 0.05 |
|  |  | Metal deactivator [13)] | 0.005 | 0.005 | 0.005 | 0.005 | 0.005 |
|  |  | Defoaming agent [14)] | 0.005 | 0.005 | 0.005 | 0.005 | 0.005 |
| Properties/ Performances | Kinematic viscosity ($mm^2/s$) | 40° C. | 42.15 | 42.05 | 42.01 | 42.37 | 42.04 |
|  |  | 100° C. | 7.15 | 7.11 | — | — | — |
|  | Viscosity index |  | 132 | — | — | — | — |
|  | Flash point [C.O.C] (° C.) |  | 282 | 264 | 231 | 234 | 233 |
|  | RBOT (min) |  | 1024 | 980 | — | — | — |
|  | Oxidation test [165.5° C., 96h][15)] Elevated value of acidic number (mgKOH/g) |  | 0.52 | 0.99 | — | — | — |
|  | 5% by mass loss-in-quantity temperature in thermal analysis (° C.) |  | 284 | 285 | 281 | 281 | 283 |
|  | 5% by mass distillation temperature in vacuum distillation (° C.) |  | 487 | 490 | 485 | 483 | 486 |

TABLE 4

Table 3-2

|  |  |  | Example |  | Comparative Example |  |
|---|---|---|---|---|---|---|
|  |  |  | 7 | 8 | 2B | 4 |
| Applied oil species |  |  | Oil impregnation bearing oil | Metalworking fluid | — | — |
| Component composition (% by mass) | Base oil | Acid catalyst PAO[1)] | — | — | 98.44 | 99.44 |
|  |  | Metallocene PAO [2)] | 98.44 | 100 | — | — |
|  | Additives | Phenol-based antioxidant [3] | — | — | 0.5 | 0.2 |
|  |  | Amine-based antioxidant 1 [4)] | — | — | 0.5 | 0.3 |
|  |  | Amine-based antioxidant 2[5)] | 0.5 | — | — | — |
|  |  | Phosphate 1 [6)] | — | — | 0.5 | — |
|  |  | Phosphate 2 [7)] | 1.0 | — | — | — |

TABLE 4-continued

Table 3-2

|  |  |  | Example | | Comparative Example | |
|---|---|---|---|---|---|---|
|  |  |  | 7 | 8 | 2B | 4 |
| Applied oil species |  |  | Oil impregnation bearing oil | Metalworking fluid | — | — |
|  | Phosphate amine [8] |  | — | — | — | — |
|  | Sulfur-based extreme pressure agent 1 [9] |  | — | — | — | — |
|  | Sulfur-based extreme-pressure agent 2 [10] |  | — | — | — | — |
|  | Metal-based extreme-pressure agent [11] |  | — | — | — | — |
|  | Rust preventing agent [12] |  | 0.05 | — | 0.05 | 0.5 |
|  | Metal deactivator [13] |  | 0.005 | — | 0.005 | 0.005 |
|  | Defoaming agent [14] |  | 0.005 | — | 0.005 | 0.005 |
| Properties/ Performances | Kinematic viscosity | 40° C. | 42.06 | 40.92 | 47.97 | 47.91 |
|  | (mm²/s) | 100°C. | — | 7.10 | 7.84 | — |
|  | Viscosity index |  | — | 135 | 132 | — |
|  | Flash point [C.O.C] (° C.) |  | 231 | 266 | 233 | 235 |
|  | RBOT (min) |  | — | 48 | 1012 | 680 |
|  | Oxidation test [165.5° C., 96h][15] Elevated value of acidic number (mgKOH/g) |  | — | — | 0.11 | 0.166 |
|  | 5% by mass loss-in-quantity temperature in thermal analysis (° C.) |  | 283 | 287 | 261 | 263 |
|  | 5% by mass distillation temperature in vacuum distillation (° C.) |  | 485 | 490 | 422 | 425 |

[Annotation]
(1) 1-decene tetramer, poly-α-olefin (manufactured by Amoco Co., Ltd., trade name "DYURASYN 164"), prepared by $BF_3$ process)
(2) Dimer, 1-decene dimer obtained in Example 1 ($C_{40}$ content: 92.7% by mass)
(3) Di-t-butyl-p-cresol
(4) Dioctyl diphenyl amine
(5) N-(p-octylphenyl)-1-naphthyl amine
(6) Tricresyl phosphate
(7) Dioleyl hydrogen phosphite
(8) Di(mono)methylacid phosphate amine
(9) Dioctyl disulfide
(10) Sulfurized fat
(11) Zinc-dithiophosphate
(12) Alkenyl succinate
(13) Benzotriazole
(14) Dimethylpolysiloxane
(15) An increased amount of acid number was measured by carrying out a test at 165.5° C. for 96 hours, based on an oxidation stability test for lubricant of internal combustion engine as described in JIS K 2514.

INDUSTRIAL APPLICABILITY

According to the present invention, a saturated aliphatic hydrocarbon compound can be selectively produced in high concentration, in which the saturated aliphatic hydrocarbon compound has a low kinematic viscosity at 40° C., a low-temperature fluidity, and a high flash point, while being excellent in low-volatility and thermal stability, and has a predetermined structure useful as a lubricant base oil.

The lubricant composition of the present invention contains the saturated aliphatic hydrocarbon compound as described above as a lubricant base oil having the above performances. The lubricant composition of the present invention can be suitably used in an internal combustion engine, a torque transmission device, a fluid coupling, a sliding bearing, a rolling bearing, an oil-containing bearing, a fluid bearing, a compression apparatus, a chain, a gear, a hydraulic pressure, a vacuum pump, clock parts, a hard disk, a refrigerating machine, a cutting operation, a rolling operation, a drawing operation, an extruding operation, a form rolling operation, a forging operation, a heat treatment, a heating medium, a shock absorber, a brake, a sealing device, an aerospace plane such as an aircraft or an artificial satellite, particularly the hydraulic pressure, the turbine, the machine tool, the gear, and the metal-working.

The invention claimed is:
1. A lubricant composition, comprising:
  (a) a saturated aliphatic hydrocarbon compound represented by formula (1):

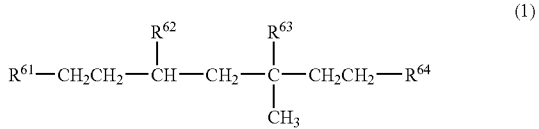

(1)

where $R^{61}$ to $R^{64}$ each represent independently a hydrogen atom or a linear or branched alkyl group having 1 to 16 carbon atoms, and the total number of carbon atoms in $R^{61}$ to $R^{64}$ is an integer of 4 to 64; and/or
(b) a saturated aliphatic hydrocarbon compound represented by formula (2):

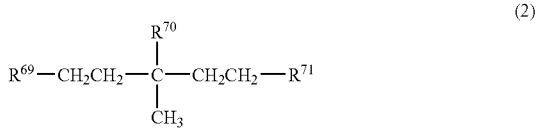

(2)

where $R^{69}$ is a linear or branched alkyl group having 4 to 6 carbon atoms, $R^{70}$ and $R^{71}$ each represent independently a hydrogen atom or a liner or branched alkyl group having 1 to 16 carbon atoms, and the total number of carbon atoms in $R^{69}$ to $R^{71}$ is an integer of 3 to 48;
wherein the saturated aliphatic hydrocarbon compound contains 11-methyl-11,13-dioctyl tricosane in an amount of 55% by mass or more,
wherein the saturated aliphatic hydrocarbon compound contains 92.5% or more by mass of hydrocarbon with 40 carbon atoms, and
wherein the content of 11-methyl-11,13 dioctyl tricosane occupied in the hydrocarbon product with 40 carbon atoms is 75% or more by mass;
wherein said saturated aliphatic hydrocarbon compound of formula (1) is prepared using an α-olefin as a raw material by a process comprising:
(I) producing a vinylidene olefin by dimerizing the α-olefin in a presence of a metallocene complex catalyst;
(II) further dimerizing the vinylidene olefin in a presence of an acid catalyst; and
(III) hydrogenating a dimer obtained by the step (II); and
(c) at least one member selected from an antioxidant, an oiliness agent, an extreme pressure agent, a detergent-dispersant, a viscosity index improver, a rust preventing agent, a metal deactivator, and an defoaming agent.

2. A lubricant composition according to claim 1, wherein the saturated aliphatic hydrocarbon compound is a compound represented by formula (1-a):

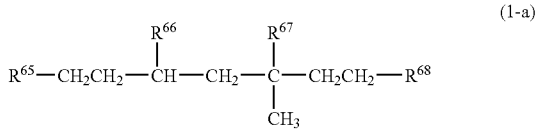

(1-a)

where $R^{65}$ to $R^{68}$ each represent independently a linear alkyl group having 8 to 16 carbon atoms.

3. A lubricant composition according to claim 2, wherein $R^{65}$ to $R^{68}$ in the general formula (1-a) each represent a linear alkyl group having 8 to 12 carbon atoms.

4. A lubricant composition according to claim 3, wherein the saturated aliphatic hydrocarbon compound contains 11-methyl-11,13-dioctyl tricosane in an amount of 55% by mass or more.

5. A lubricant composition according to claim 4, wherein a content of 11-methyl-11,13-dioctyl tricosane occupied in the saturated aliphatic hydrocarbon compound having 40 carbon atoms is 65% by mass or more.

6. A lubricant composition according to claim 1, further comprising at least one component selected from the group consisting of an antioxidant, an oiliness agent, an extreme pressure agent, a detergent-dispersant, a viscosity index improver, a rust preventing agent, a metal deactivator, and an defoaming agent.

7. A lubricant composition according to claim 1, which is used in hydraulic pressure, turbine, working machine, bearing, gear, or metal-working.

8. A bearing oil, comprising the lubricant composition according to claim 1.

9. A bearing comprising the bearing oil according to claim 8.

10. A bearing according to claim 9, further comprising a dynamic pressure fluid dynamic bearing, an oil-containing bearing, or an oil-containing bearing provided with a dynamic pressure groove.

11. A gyral equipment comprising a bearing unit including a bearing according to claim 9.

12. The lubricant composition of claim 1 comprising:
a saturated aliphatic hydrocarbon compound represented by formula (1):

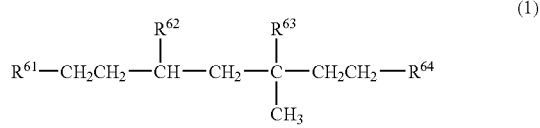

(1)

where $R^{61}$ to $R^{64}$ each represent independently a hydrogen atom or a liner or branched alkyl group having 1 to 16 carbon atoms, and the total number of carbon atoms in $R^{61}$ to $R^{64}$ is an integer of 4 to 64.

13. The lubricant composition of claim 1 comprising:
a saturated aliphatic hydrocarbon compound represented by formula (2):

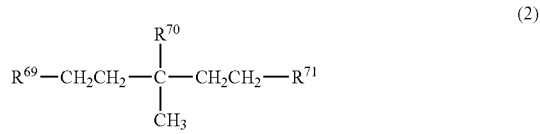

(2)

where $R^{69}$ is a linear or branched alkyl group having 4 to 6 carbon atoms, $R^{70}$ and $R^{71}$ each represent independently a hydrogen atom or a liner or branched alkyl group having 1 to 16 carbon atoms, and the total number of carbon atoms in $R^{69}$ to $R^{71}$ is an integer of 3 to 48.

14. The lubricant composition of claim 1 that comprises a compound of formula (1) and a compound of formula (2).

15. The lubricant composition of claim 1 that has a higher low-temperature fluidity, low evaporativity, thermal stability, and/or oxidation stability compared to an otherwise identical lubricant composition prepared with a Ziegler catalyst.

16. A method of making the lubricant composition of claim 1, comprising combining (a) and/or (b) and (c).

17. A method of lubricating a bearing, comprising applying the lubricant of claim 1 to the bearing.

* * * * *